US006127166A

United States Patent [19]
Bayley et al.

[11] Patent Number: 6,127,166
[45] Date of Patent: Oct. 3, 2000

[54] MOLLUSCAN LIGAMENT POLYPEPTIDES AND GENES ENCODING THEM

[76] Inventors: Hagan Bayley, 1800 Springbrook Estates Dr., College Station, Tex. 77845; Qiuping Cao, 15 Sandpiper Dr., Shrewsbury, Mass. 01545; Yunjuan Wang, 4300 Boyett St., Bryan, Tex. 77801

[21] Appl. No.: 08/963,168

[22] Filed: Nov. 3, 1997

[51] Int. Cl.$^7$ .............................. C12N 1/20; C12N 15/00; C12P 21/06; C07H 21/02
[52] U.S. Cl. .................. 435/252.3; 435/69.1; 435/320.1; 435/325; 536/23.1; 536/23.5
[58] Field of Search ............................... 435/69.1, 320.1, 435/325, 252.3; 536/23.1, 23.5

[56] References Cited

U.S. PATENT DOCUMENTS

| | | | |
|---|---|---|---|
| 4,132,746 | 1/1979 | Urry et al. | 260/857 TW |
| 4,187,852 | 2/1980 | Urry et al. | 128/334 R |
| 4,474,851 | 10/1984 | Urry | 428/373 |
| 4,500,700 | 2/1985 | Urry | 528/328 |
| 4,589,882 | 5/1986 | Urry | 623/11 |
| 4,783,523 | 11/1988 | Urry et al. | 530/323 |
| 4,870,055 | 9/1989 | Urry et al. | 514/12 |
| 4,898,926 | 2/1990 | Urry | 528/328 |
| 5,064,430 | 11/1991 | Urry | 623/1 |
| 5,250,516 | 10/1993 | Urry | 514/17 |
| 5,336,256 | 8/1994 | Urry | 623/1 |
| 5,519,004 | 5/1996 | Urry | 514/17 |
| 5,527,610 | 6/1996 | Urry | 428/373 |
| 5,606,019 | 2/1997 | Cappello | 530/329 |
| 5,674,290 | 10/1997 | Li | 623/11 |

OTHER PUBLICATIONS

Alexander (1966), Rubber–Like Properties of the Inner Hinge–Ligament of Pectinidae, *J. Exp. Biol.* 44:119–130.
Andersen (1967), Isolation of a New Type of Cross Link from the Hinge Ligament Protein of Molluscs, *Nature* 216:1029–1030.
Andersen et al. (1964), Resilin: a Rubberlike Protein in Arthropod Cuticle, *Adv. in Insect Physiol.* 2:1–65.
Bailey et al. (1961), Amino Acid Composition of a New Rubber–like Protein, Resilin, *Biochimica Biophys. Acta* 48:452–459.
Barro et al. (1997) Transformation of Wheat with High Molecular Weight Subunit Genes Results in Improved Functional Properties, *Nature Biotechnology* 15:1295–1299.
Beckwitt et al. (1994), Sequence Conservation in the C–terminal Region of Spider Silk Proteins (Spidroin) from Nephila clavipes (Tetragnathidae) and Araneus bicentenarius (Araneidae), *J. Biol. Chem.* 269:6661–6663.
Coles (1966), Studies on Resilin Biosynthesis. *J. Insect. Physiol.* 12:679–691.
Coyne et al. (1997), Extensible Collagen in Mussel Byssus: A Natural Block Copolymer, *Science* 277:1830–1832.
Dagani (1995), Polymeric Smart Materials Respond to Changes in Their Environment, *Chem. Eng. News*, Sep. 18, 1995, 30–33.

Dickinson et al., (1995), Muscle Efficiency and Elastic Storage in the Flight Motor of Drosophila, *Science*, 268:87–90.
Engel (1997), Versatile Collagens in Invertebrates, *Science* 277: 1785–1786.
Erickson (1997), Stretching Single Protein Molecules: Titin is a Weird Spring, *Science* 276:1090–1092.
Guerette et al. (1996), Silk Properties Determined by Gland–Specific Expression of a Spider Fibroin Gene Family, *Science* 272:112–114.
Hare (1963), Amino Acids in the Proteins from Aragonite and Calcite in the Shells of Mytilus Californianus, *Science* 139:216–217.
Hinman et al. (1992), Isolation of a Clone Encoding a Second Dragline Silk Fibroin, *J. Biol. Chem.* 267:19320–19324.
Kahler et al. (1976), The Chemical Composition and Mechanical Properties of the Hinge Ligament in Bivalve Molluscs, *Biol. Bull.* 151:161–181.
Keller (1997), Muscle Structure: Molecular Bungees, *Nature* 387:233–235.
Kellermeyer et al. (1997), Folding–Unfolding Transitions in Single Titin Molecules Characterized with Laser Tweezers, *Science* 276:1112–1116.
Kelly et al. (1967), Abductin: A Rubber–Like Protein from the Internal Triangular Winge Ligament of Pecten, *Science* 155:208–210.
Kikuchi et al. (1981), Methionine Sulfoxide in the Resilium of Surf Clams, *J. Biochem.* 89:1975–1976.
Libeit et al., (1995), Titins: Giant Proteins in Charge of Muscle Ultrastructure and Elasticity, *Science* 270:293–296.
Laursen (1992), Reflections on the Structure of Mussel Adhesive Proteins, *In Results and Problems in Cell Differentiation 19 Biopolymers*, Case S.T. (ed), Springer–Verlag: Berlin Heidelberg, 55–74.
Laursen et al. (1990), Characterization and Structure of Mussel Adhesive Proteins, *Mat. Res. Soc. Symp. Proc.* 174:237–242.
Lombardi et al. (1993), Preliminary Characterization of Resilin Isolated from the Cockroach, Periplaneta Americana, *MRS Symp. Proc.* 292:3–7.

(List continued on next page.)

Primary Examiner—Rebecca E. Prouty
Assistant Examiner—M. Monshipouri
Attorney, Agent, or Firm—Fish & Richardson P.C.

[57] ABSTRACT

The invention provides substantially pure abductin protein and polypeptides, polypeptides composed of multiple repeats of the glycine-rich repeat sequences of abductin, and hybrid polypeptides containing an abductin polypeptide linked to another protein or polypeptide, e.g., an elastin or fibroin (silk) polypeptide, as well as nucleic acids encoding these polypeptides. The abductin polypeptides and their derivatives can be used in the manufacture of a broad range of biomaterials ranging from light-weight durable fabric for clothing to matrices useful for human tissue and organ prostheses.

22 Claims, 2 Drawing Sheets

OTHER PUBLICATIONS

Lotz (1974), Crystal Structure of Polyglycine *J. Mol. Biol.* 87:169–180.

Malencik et al. (1996), Dityrosine: Preparation, isolation, and Analysis, *Anal. Biochem.* 242:202–213.

McPherson et al. (1992), Production and Purification of a Recombinant Elastomeric Polypeptide, G–(VPGVG)19–VPGV, from Escherichia coli, *Biotechnol. Prog.* 8:347–352.

Meenakshi et al. (1969), The Chemical Composition of the Periostracum of the Molluscan Shell, *Comp. Biochem. Physiol.* 29:611–620.

Pattanaik et al. (1991), Phosphorylation and Dephosphorylation Modulation of an Inverse Temperature Transition, *Biochem. Biophys. Res. Commun.* 178:539–545.

Poirier et al. (1995), Production of Polyhydroxyalkanoates, a Family of Biodegradable Plastics and Elastomers in Bacteria and Plants, *Biotechnology* 13:142–150.

Prince et al. (1995), Construction, Cloning, and Expression of Synthetic Genes Encoding Spider Dragline Silk. *Biochemistry* 34:10879–10885.

Rief et al. (1997), Reversible Unfolding of Individual Titin Immunoglobulin Domains by AFM, *Science* 276:1109–1112.

Ringsdorf (1996), Riding Tandems with Nature, *Nature* 382:299–300.

Sastry (1965), The Development of External Morphology of Pelagic Larval and Post–Larval Stages of the Bay Scallap, Aequipecten Irradians Concentricus Say, Reared in the Laboratory, *Bull. Mar. Sci.* 15:417–435.

Shewry et al. (1995), Biotechnology of Breadmaking: Unraveling and Manipulating the Multi–Protein Gluten Gluten Complex, *Biotechnology* 13:1185–1190.

Sudo et al. (1997), Structures of Mollusc Shell Framework Proteins, *Nature* 387:563–564.

Tanaka (1981), Gels, *Sci. Am.* Jan., 124–138.

Thornhill (1971), Abductin, Locus and Spectral Characteristics of a Brown Fluorescent Chromophore, *Biochemistry* 10:2644–2649.

Tirrell et al. (1994), Biomolecular Materials, *Chem. Eng. News* Dec. 19. 1994, 40–51.

Tirrell (1996), Putting a New Spin on Spider Silk, *Science* 271:39–40.

Tskhovrebova et al. (1997), Elasticity and Unfolding of Single Molecules of the Giant Muscle Protein Titin. *Nature* 387:308–312.

Urry (1993), Molecular Machines: How Motion and Other Functions of Living Organisms Can Result from Reversible Chemical Changes, *Angew. Chem. Int. Ed. Engl.* 32:819–841.

Urry (1995), Elastic Biomolecular Machines, *Scientific American* Jan., 64–69.

Urry et al. (1996), Transductional Protein–Based Polymers as New Controlled–Release Vehicles, In Controlled Drug Delivery: the Next Generation, K. Park, ed. (*Amer. Chem. Soc.: Professional Reference Book*),405–437.

Urry et al. (1995), Nonlinear Mechanical Force Induced pKa Shifts: Implications for Efficiency of Conversion to Chemical Energy, *J. Am. Chem. Soc.* 117:8478–8479.

Urry et al. (1995), Electro–chemical Transduction in Elastic Protein–Based Polymers, *Biochem. Biophys. Res. Commun.* 210:1031–1039.

Urry et al. (1976), Synthetic, Cross–Linked Polypentapeptide of Tropoelastin: Anisotropic, Elastomer, *Biochemistry* 15:4083–4089.

Urry et al. (1985), Polypentapeptide of Elastin: Temperature Dependence of Ellipticity and Correlation with Elastomeric Force, *Biochem. & Biophys. Res. Commun.* 130:50–57.

Urry et al. (1992), Design at Nanotric Dimensions to Enhance Hydrophobicity–Induced pKa Shifts, *J. Am. Chem. Soc.* 114:8716–17.

Vincent (1991), Proteins, Chapter 2 In Structural Biomaterials (Revised edition) (*Princeton, NJ: Princeton University Press*), 37–72 and 224–236.

Vogel (1997), Squirt Smugly, Scallop, *Nature* 385:21–22.

Waite et al. (1985), Peptide Repeats in a Mussel Glue Protein: Theme and Variations, *Biochem.* 24:5010–5014.

Wrigley (1996), Giant Proteins with Flour Power, *Nature* 381:738–739.

Ap7
```
ATGAACGCCT ACATCTGTCT TGCTGCTTGT CTGATCGCTG CTGTCAGCGC CGCCGGATAC
GGAGGCGGTG CCGGAAGTAT GGGCGGTACC GGAGGAATGG GAGGCGGAAT GAACGCAGGC
GGATTCGGCG GTATGGGCGG AGGAATGGGC GGAGGTAAAG GCGGATTCGG CGGAATAGGC
GGATTCGGCG GCATGGGAGG TGGAATGGGT GGAGGTCCAG GCGGATTCGG TGGAATGGGA
GGTTTCGGCG GAATGGGCGG CGGGAAAGGT GGATTCGGGG GAATGGGCAG TGGTATGGGA
GGTTTCGGAG GAATGGGAGG CGGAAATGCC GGTTTCGGCG GAATGGGAGG CGGCAATGCC
GGATTCGGTG GAATGGGCGG CCAAGGTGGA TTTGGCGGAA AAGGCTATTA A (SEQ ID
NO:2)
```

Ap4
```
ATGAACGCCT ACATCTGTCT TGCTGCTTGT CTGATCGCTG CTGTCAGCGC CGCCGGATAC
GGAGGCGGTG CCGGAAGTAT GGGCGGTACC GGAGGAATGG GAGGCGGAAT GAACGCAGGC
GGATTCGGCG GTATGGGCGG AGGAATGGGC GGAGGTAAAG GCGGATTCGG CGGAATAGGC
GGATTCGGCG GCATGGGAGG TGGAATGGGT GGAGGTCCAG GCGGATTCGG TGGAATGGGA
GGTTTCGGCG GAATGGGCGG CGGGAAAGGT GGATTCGGAG GAATGGGCAG TGGTATGGGA
GGTTTCGGAG GAATGGGAGG CGGAAATGCC GGTTTCGGCG GAATGGGAGG CGGCAATGCC
GGATTCGGTG GAATGGGCGG CCAAGGTGGA TTTGGCGGAA AAGGCTATTA A (SEQ ID
NO:1)
```

Ap5
```
ATGAACGCCT ACATCTGTCT TTCTGCTTGT CTTATCGCTG CTGTCAGCGC CGCCGGATAC
GGAGGTGGTG CCGGAAGTAT GGGCGGTACC GGAGGAATGG GAGGCGGAAT GAACGCAGGC
GGATTCGGCG GTATGGGCGG AGGAATGGGC GGAGGTAAAG GCGGATTCGG CGGAATGGGC
GGATTCGGCG GCATGGGAGG TGGAATGGGC GGAGGTCCAG GCGGATTCGG TGGAATGGGA
GGTTTCGGAG GAATGGGTGG CGGAAAAGGT GGATTCGGAG GAATGGGCAG TGGTATGGGA
GGTTTCGGAG GAATGGGAGG CGGAAATGCC GGTTTCGGTG GAATGGGCGG CCAAGGTGGA
TTTGGCGGAA AAGGTTATTA A (SEQ ID NO:3)
```

Ap9
```
ATGAACGCCT ACATCTGTCT TGCTGCTTGT CTGATCGCTG CTGTCAGCGC CGCCGGATAC
GGAGGCGGTG CCGGAAGTAT GGGCGGTACC GGAGGAATGG GAGGCGGAAT GAACGCAGGC
GGATTCGGCG GTATGGGCGG AATGGGCGGA GGTAAAGGCG GATTCGGCGG AATAGGCGGC
TTCGGAGGTG GTATGGGTGG AGGTCCAGGC GGATTCGGTG GAATGGGAGG TTTCGGCGGA
ATGGCGGCGA AAGGTGGATT CGGAGGAATG GGCAGTGGTA TGGGAGGTTT CGGAGGAATG
GGAGGCGGAA ATGCCGGTTT CGGCGGAATG GGAGGCGGCA ATGCCGGATT CGGTGGAATG
GGCGGCCAAG GTGGATTTGG CGGAAAAGGC TATTAA (SEQ ID NO:4)
```

Ap12
```
ATGAACGCCT ACATCTGCCT TGCTGCTTGT CTTATTGCTG TAGTCAGTGC CGCCGGATAC
GGAGGCGGTG CCGGAAGTAT GGGCGGTACC GGCGGAATGG GAGGTGGAAT GAACGCAGGC
GGATTCGGCG GTATTGGCGG AGGAATGGGC GGAGGTAAAG GAGGATTCGG CGGAATGGGC
GGAGGTCCAG GTGGATTCGG CGGAATTGGC GGAGGTTCAG GTGGATTCGG TGGAATGGGA
GGTTTCGGCG GAATGGGCGG CGGAAAAGGT GGATTCGGAG GAATGGGCAG TAGCATGGGA
GGTTTCGGAG GAATGGGAGG CGGAAATGCC GGTTTCGGTG GAATGGGCGG TCAAAGTGGA
ATGGGCGGTC AAAGTGGATT TGGCGGCAAA GGTTATTAA (SEQ ID NO:5)
```

Fig. 1

```
              10         20         30         40         50
Ap4/7   MNAYICLAAC LIAAVSAAGY GGGAGSMGGT GGMGGGMNAG GFGGMGGGMG
Ap5     MNAYICLSAC LIAAVSAAGY GGGAGSMGGT GGMGGGMNAG GFGGMGGGMG
Ap9     MNAYICLAAC LIAAVSAAGY GGGAGSMGGT GGMGGGMNAG GFGGMGG-MG
Ap12    MNAYICLAAC LIAVVSAAGY GGGAGSMGGT GGMGGGMNAG GFGGIGGGMG 60         70         8          90        100
        GGKGGFGGIG GFGGMGGGMG GGPGGFGGMG GFGGMGGGKG GFGGMGSGMG
        GGKGGFGGMG GFGGMGGGMG GGPGGFGGMG GFGGMGGGKG GFGGMGSGMG
        GGKGGFGGIG GF---GGGMG GGPGGFGGMG GFGGMAA-KG GFGGMGSGMG
        GGKGGFGGMG GGPGGFGGIG GGSGGFGGMG GFGGMGGGKG GFGGMGSSMG 110        120        130
        GFGGMGGGNA GFGGMGGGNA GFGGMGGQGG FGGKGY    (SEQ ID NO:6)
        GFGGMGGGNA GFGGMGG--- ------QGG FGGKGY    (SEQ ID NO:7)
        GFGGMGGGNA GFGGMGGGNA GFGGMGGQGG FGGKGY   (SEQ ID NO:8)
        GFGGMGGGNA GFGGMGG--- -QSGMGGQSG FGGKGY   (SEQ ID NO:9)

Fig. 2
```

MOLLUSCAN LIGAMENT POLYPEPTIDES AND GENES ENCODING THEM

This invention was made in part with government support under grant number DAAH04-94-2-0002 awarded by the Army Research Office. The United States government may have certain rights in the invention.

BACKGROUND OF THE INVENTION

The invention relates to a resilient molluscan protein, corresponding polypeptides, and nucleic acids encoding the same.

The inner hinge ligament of bivalve molluscs opposes the action of the adductor muscles. This arrangement permits the opening and closing of the shell. In scallops, the apparatus has evolved for swimming (Vogel, Nature, 385:21, 1997). By opening and closing their shells about four times per second, scallops swim a few meters at a time to escape slow-moving predators such as starfish. The scallop ligament is almost entirely protein and its relatively low extent of mineralization compared to the ligaments of other molluscs is thought to contribute to its high resilience (96% recovered work), which is extraordinary even by molluscan standards (Kahler et al., Biol. Bull., 151:161, 1976). The major component of all inner hinge ligaments is the protein abductin (Kelly et al., Science, 155:208, 1967). The physical properties of the ligament suggest that the resilience is entropy based (Alexander, J. Exp. Biol., 44:119, 1966) and that abductin is lightly crosslinked (Anderson, Nature, 216:1029, 1967; Thornhill, Biochemistry, 10:2644, 1971).

SUMMARY OF THE INVENTION

The invention is based on the discovery of a substantially pure abductin protein and polypeptides, polypeptides composed of multiple repeats of the glycine-rich repeat sequences of abductin, and hybrid polypeptides containing an abductin polypeptide linked to another protein or polypeptide, e.g., an elastin or fibroin (silk) polypeptide, as well as nucleic acids encoding these polypeptides. The abductin polypeptides and their derivatives can be used in the manufacture of a broad range of biomaterials ranging from light-weight durable fabric for clothing to matrices useful for human tissue and organ prostheses. As will be clear from the disclosure below, it is possible by routine experimentation to make abductin-based biomaterials suitable for all these applications.

Specifically, the invention features a substantially pure nucleic acid molecule encoding a bay scallop (Argopecten) hinge ligament polypeptide, i.e., abductin. This nucleic acid molecule can have a sequence that is at least 50% identical (e.g., 75, 85, 90, 95, 99, or 100% identical) to the sequence of SEQ ID NOS:1, 2, 3, 4, or 5. The sequence can encode polypeptides including the amino acid sequences of SEQ ID NOS:6, 7, 8, or 9. The invention also includes a substantially pure nucleic acid molecule that hybridizes under stringent conditions to a nucleic acid molecule including the sequence of SEQ ID NOS:1, 2, 3, 4, or 5, or the complement thereof.

The invention also encompasses substantially pure nucleic acid molecules containing sequences encoding the abductin repeat polymers and hybrid abductin molecules described below.

A "substantially pure nucleic acid molecule" is a nucleic acid molecule that is free of other nucleic acid molecules, e.g., genes which, in the naturally occurring genome of the organism from which the new nucleic acid molecule is derived, flank the gene of interest. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences.

A nucleic acid molecule which is "substantially identical" to a given reference nucleic acid molecule is a nucleic acid molecule having a sequence that has at least 85%, preferably 90%, and more preferably 95%, 99% or more identity to the sequence of the given reference nucleic acid molecule, e.g., the nucleic acid sequence of SEQ ID NOS:1–5.

Where a particular nucleic acid molecule is said to have a specific percent identity to a reference nucleic acid molecule of a defined length, the percent identity is relative to the reference nucleic acid molecule. Thus, a nucleic acid molecule that is 50% identical to a reference nucleic acid molecule that is 100 nucleotides long can be a 50 nucleotide that is completely identical to a 50 nucleotide long portion of the reference nucleic acid molecule. It might also be a 100 nucleotide long nucleic acid molecule which is 50% identical to the reference nucleic acid molecule over its entire length. Of course, other nucleic acid molecule will meet the same criteria.

The length of the reference nucleic acid sequence will generally be at least 50, preferably at least 60 nucleotides, more preferably at least 75 nucleotides, and most preferably at least 100 nucleotides or at least 300 or more nucleotides.

Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

The abductin nucleic acid molecules include: (a) nucleic acid molecules having the sequence of SEQ ID NOS:1, 2, 3, 4, or 5; (b) nucleic acid molecules that encode a polypeptide with the amino acid sequences with SEQ ID NOS: 6, 7, 8, or 9, the abductin repeat polymers containing two or more glycine-rich repeat monomers, and the hybrid abductin molecules described herein; (c) any nucleotide sequences that hybridize to the complement of the DNA sequences with SEQ ID NOS:1, 2, 3, 4, or 5 under stringent conditions, i.e., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., Current Protocols in Molecular Biology, Vol. I, Green Publishing Associates, Inc., and John Wiley & sons, Inc., New York, 1989), and encode functionally active gene products; and (d) any nucleotide sequence that hybridizes to the complement of the DNA sequences that encode polypeptides having the amino acid sequences with SEQ ID NOS:5, 6, 7, or 8, abductin repeat polymers, and hybrid abductin molecules under stringent conditions. The invention also includes degenerate variants of sequences (a) through (d).

The invention also includes nucleic acid molecules, preferably DNA molecules, that under stringent conditions hybridize to, and are therefore the complements of, the nucleotide sequences (a) through (d), in the preceding paragraph. Such hybridization conditions may be stringent, as described above, or less stringent, such as moderately stringent conditions. For example, moderately stringent hybridization conditions include washes in 0.2 ×SSC/0.1% SDS at 42° C. (Ausubel et al., cited supra).

In instances wherein the nucleic acid molecules are deoxyoligonucleotides ("oligos"), highly stringent conditions refer to washing in 6×SSC/0.05% sodium pyrophosphate at 37° C. (for 14-base oligos), 48° C. (for 17-base oligos), 55° C. (for 20-base oligos), and 60° C. (for 23-base oligos).

The new nucleic acid molecules encode abductin polypeptides or are complementary to an abductin coding strand (i.e., antisense molecules) useful, for example, in abductin gene regulation and/or as antisense primers in amplification reactions of abductin nucleic acid sequences. Still further, such molecules can be used as components of screening methods whereby, for example, the presence of a particular abductin allele, may be detected.

In addition to the nucleotide sequences described above, full length genomic sequences can be identified and readily isolated, without undue experimentation, by molecular biological techniques well known in the art. The invention encompasses these nucleic acid molecules.

The invention also encompasses: (a) DNA vectors that contain any of the abductin polypeptides, abductin repeat polymers, and hybrid abductin molecules coding sequences recited above and/or their complements (i.e., antisense); and (b) DNA expression vectors that contain any of these coding sequences. An expression vector is composed of or contains a nucleic acid in which a polynucleotide sequence encoding a peptide or polypeptide of the invention is operatively linked to a promoter or enhancer-promoter combination. A promoter is a transcriptional regulatory element composed of a region of a DNA molecule typically within 100 nucleotide pairs in front of (upstream of) the point at which transcription starts.

Another transcriptional regulatory element is an enhancer, which provides specificity in terms of time, location, and expression level. Unlike a promoter, an enhancer can function when located at variable distances from the transcription site, provided a promoter is present. An enhancer can also be located downstream of the transcription initiation site. A coding sequence of an expression vector is operatively linked to a transcription terminating region.

To bring a coding sequence under control of a promoter, it is necessary to position the translation initiation site of the translational reading frame of the peptide or polypeptide between one and about fifty nucleotides downstream (3') of the promoter. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Expression vectors and methods for their construction are known to those familiar with the art (Ausubel et al., cited supra). Suitable vectors include plasmids, and viral vectors such as herpes viruses, retroviruses, canary pox viruses, adenoviruses and adeno-associated viruses, among others.

A gene and regulatory sequences are "operably linked" when they are connected in such a way as to permit gene expression when the coding sequence (e.g., the abductin coding sequence) of the gene is bound to the regulatory sequences, e.g., within an expression vector.

The invention includes cell lines transfected with expression vectors containing the sequences encoding the new abductin polypeptides, abductin repeat polymers, and hybrid abductin molecules. Cells to be used for transfection include, but are not restricted to, bacteria such as E. coli and B. subtilis, Sf9 insect cells, or human mammalian cells such as murine fibroblasts, murine L cells, HEK293 cells and COS cells. Cells are transfected by a variety of methods commonly used in the art, for example, electroporation or calcium phosphate precipitation. Genes can also be introduced into the cells by transduction with viral vectors, e.g., retroviruses. Successfully transfected cell lines are selected by appropriate means familiar to those of average skill in the art, e.g., using tissue culture medium supplemented with a drug such as Geneticin™ (G418) for which the relevant expression vector contains a resistance gene. Successfully transfected cell lines are screened for production of the protein of interest, e.g., abductin by a variety of possible methods, e.g., ELISA using an antibody that specifically recognizes the protein.

In another aspect, the invention features a substantially pure abductin polypeptide, e.g., encoded by a nucleic acid molecule that is at least 50% identical (e.g., 75, 85, 90, 95, 99, or 100% identical) to a sequence of SEQ ID NOS:1, 2, 3, 4, or 5. The polypeptide can include an amino acid sequence of SEQ ID NOS:6, 7, 8, or 9. Polypeptides corresponding to: (a) a first domain (SEQ ID NOS:11 and 12) of polypeptides with amino acid sequences of SEQ ID NOS:6–8 and SEQ ID NO:9, respectively; and (b) a second domain (SEQ ID NOS:13–16) of polypeptides with amino acid sequences of SEQ ID NOS:6–9, respectively, are included in the invention.

The invention also includes a series of polypeptides (SEQ ID NOS:17–21) derived by chemical digestion of bay scallop hinge ligaments with, e.g., HCl or CN—Br.

In another embodiment, the invention features a substantially pure polypeptide (e.g., an "abductin repeat polymer") containing multiple copies of a glycine rich consensus repeat sequence ("monomer units") of from three amino acid residues to a full-length polypeptide derived from the sequence of SEQ ID NOS:6, 7, 8, or 9. The polypeptides can be of varying lengths, e.g., they can contain two to five hundred copies of a monomer unit, an example of which is the abductin repeat sequence Gly-Gly-Phe-Gly-Gly-Met-Gly-Gly-Gly-X (SEQ ID NO:10), where X can be any amino acid, and is preferably Lys, Met, or Asn. The polypeptides can contain one or more abductin repeat monomer units; additional monomeric units can be the same or different in amino acid sequence or in length, e.g., an abductin monomer unit can contain three to fifty amino acid residues of the amino acid sequence of naturally-occurring abductin. These abductin repeat polymers can be optionally cross-linked.

The invention also feature a copolymer (hybrid abductin molecule) containing one or more copies of an abductin polypeptide and one or more copies of a non-abductin component. The abductin polypeptide can be an abductin fragment containing a glycine rich abductin repeat sequence, e.g., Gly-Gly-Phe-Gly-Gly-Met-Gly-Gly-Gly-X (SEQ ID NO:10) or a full-length polypeptide with the sequence of SEQ ID NOS:6, 7, 8, or 9; the polypeptide can optionally be cross-linked. The non-abductin component can be full-length fibroin, or a fragment (i.e., a fibroin-derived repeat sequence) of fibroin, e.g., Gly-Ala-Gly-Ala-Ser (SEQ ID NO:23), Ala-Ser-Ala-Ala-Ala-Ala-Ala-Ala (SEQ ID NO:24), Ser-Ser-Ala-Ala-Ala-Ala-Ala-Ala-Ala (SEQ ID NO:25), or Ala-Ala-Ala-Ala-Ala-Ala-Ala-Ala (SEQ ID NO:26).

The hybrid abductin molecule can contain several different non-abductin components. For example, the fibroin hybrid abductin molecule can in addition contain multiple copies of an elastin repeat sequence, e.g., Val-Pro-Gly-Val-Gly (SEQ ID NO:27), Val-Pro-Ala-Val-Gly (SEQ ID NO:28), Val-Pro-Gly-Gly (SEQ ID NO:29), or Ile-Pro-Gly-Val-Gly (SEQ ID NO:30), wherein the amino-terminal Ile is linked to Pro-Gly-Val-Gly (SEQ ID NO:31), Gly-Val-Gly, Val-Gly, Gly, or a covalent bond, and the carboxy-terminal Gly is linked to Ile-Pro-Gly-Val (SEQ ID NO:32), Ile-Pro-Gly, Ile-Pro, Ile, or a covalent bond.

Collagen or a functional collagen fragment (e.g., a collagen-derived repeat sequence) thereof, e.g., Gly-Pro-Hyp, where Hyp is hydroxyproline, can also be used as a non-abductin component. A hybrid abductin molecule can also be made using a mussel adhesin or a functional fragment thereof. Examples of functional adhesin fragments (e.g., repeat sequences) include Ala-Lys-Pro-Ser-Tyr-Hyp-Hyp-Thr-DOPA-Lys (SEQ ID NO:33), Arg-Lys-Pro-Ser-Tyr-Hyp-Hyp-Thr-DOPA-Lys (SEQ ID NO:34), Arg-Lys-Ile-Ser-Tyr-Hyp-Hyp-Thr-DOPA-Lys (SEQ ID NO:35), Arg-Lys-Thr-Ser-Tyr-Hyp-Hyp-Thr-DOPA-Lys (SEQ ID NO:36), Gly-Lys-Pro, Ala-Lys-Pro, Gly-Gln-Gln-Lys-Gln (SEQ ID NO:37), and Gly-Gly-Val-Gln-Lys (SEQ ID NO:38), where Hyp is hydroxyproline, and DOPA is (3,4-dihydroxyphenyl)-L-alanine.

In another embodiment, the invention features a useful hybrid abductin molecule containing an enzyme or a functional fragment thereof. Such an enzyme can be a full length beta-lactam-acylase, a full-length-lipase, or functional fragments thereof containing the active sites of these enzymes. A synthetic polymer (e.g., a polyamide, a polyester, a polyvinyl, a polyethylene, a polyurethane, a polyether or a polyimide) can also be used as a component of a hybrid abductin molecule.

A "substantially pure abductin polypeptide" is an abductin polypeptide which is substantially free of other proteins, lipids, carbohydrates or other materials with which it is naturally associated.

Where a particular polypeptide is said to have a specific percent identity to a reference polypeptide of a defined length, the percent identity is relative to the reference polypeptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, other polypeptides will meet the same criteria. For the abductin polypeptides, the length of the reference polypeptide sequence will generally be at least 50 amino acids, preferably 100 amino acids and more preferably full length. Sequence identity can be measured using sequence analysis software (the Sequence Analysis Software Package of the Genetics Computer Group, University of Wisconsin Biotechnology Center, 1710 University Avenue, Madison, Wis. 53705), with the default parameters as specified therein.

The invention also features a biomaterial containing an abductin polypeptide, a fusion protein containing an abductin polypeptide and a fibroin polypeptide, or a copolymer containing multiple copies of an abductin polypeptide and multiple copies of a fibroin polypeptide. In the copolymer, the abductin polypeptide can be full-length abductin or a glycine-rich repeat sequence from abductin and the fibroin polypeptide can be full-length fibroin or a fragment of full-length fibroin. These biomaterials can be used in the manufacture, for example, of fabrics woven from threads containing the described biomaterials. Alternatively, the fabric is not woven, e.g., made of non-woven filaments, or extruded or pressed into sheets rather than filaments or threads. Methods of making threads and fabrics from synthetic polymers are known in the art.

Also included in the invention are antibodies, e.g., monoclonal, polyclonal, and engineered antibodies, which specifically bind abducting. An antibody that "specifically binds" is one that recognizes and binds to a particular antigen, e.g., an abductin polypeptide, but which does not substantially recognize or bind to other molecules.

As used herein, "abductin activity" means resilience (elasticity) that is at least 50% of the resilience of naturally occurring abductin, e.g., 75, 80, 90, 95, or 99 or 100% of the resilience of abductin.

The terms "protein" and "polypeptide" are used herein to described any chain of amino acids, regardless of length, post-translational modification (for example, glycosylation or phosphorylation) or use of uncommon amino acids such as hydroxyproline (Hyp) or dihydroxyphenylalanine (DOPA). Thus, the term "abductin polypeptides" includes the substantially purified full-length, naturally occurring abductin protein, as well as recombinantly or synthetically produced polypeptides and peptides that correspond to a full-length naturally occurring abductin protein or to particular domains or fragments of the naturally occurring protein.

An "abductin repeat polymer" is a polymer containing from about two to about five hundred copies of a monomer that contains at least three consecutive amino acids of the naturally-occurring abductin polypeptide.

A "hybrid abductin molecule" is a synthetic copolymer containing one or multiple copies of an abductin polypeptide, linked to one or multiple copies of a non-abductin component, or a functional fragment thereof. Examples of non-abductin components include fibroin, collagen, elastin, adhesin, enzymes such as penicillin acylases and lipases, and a range of synthetic polymers such as polyamides, polyesters, polyvinyls, polyethylenes, polyurethanes, polyethers or polyimides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples described herein are illustrative only and not intended to be limiting.

Other features and advantages of the invention, e.g., manufacture of resilient biomaterials, will be apparent from the following detailed description, from the drawings, and from the claims.

BRIEF DESCRIPTION OF THE DRAWINGS

FIG. 1 is a schematic representation of the nucleotide sequences of the open reading frames of five cDNA clones encoding bay scallop abductin polypeptides.

FIG. 2 is a schematic representation of the amino acid sequences of the five abductin polypeptides encoded by the cDNA clones illustrated in FIG. 1.

DETAILED DESCRIPTION

The invention features substantially pure abductin polypeptides as well as nucleic acids encoding these polypeptides. The abductin polypeptides and their derivatives can be used in the manufacture of a broad range of biomaterials ranging from light-weight durable filaments or threads, which can be woven into fabric for clothing, to matrices, which can be used as human tissue and organ prostheses.

Properties of Abductin

Resilient abductin-derived (i.e., elastic) polypeptides and their derivatives have a wide variety of applications in biomedicine and biotechnology, e.g., in the manufacture of resilient tissue prostheses and threads for fabrics. Argopecten abductin is to date the most resilient protein for which a gene has been cloned.

Described below in Example 1 is the method by which five full-length cDNA clones encoding abductin were cloned. The nucleotide sequences of the open reading frames of these clones are shown in FIG. 1. Two (Ap4 and Ap7) differ by only one nucleotide at position 279 (SEQ ID NO:1 and SEQ ID NO:2). The other three (Ap5, Ap9, and Ap12) (SEQ ID NOS:3–5) are very closely related and may represent abductin gene family members or alleles from the population of animals used to construct the cDNA library.

Abductin protein has a relatively disordered secondary structure containing repeating sequences. Central to its mechanical properties is the ability of the repeating sequences contained within the polypeptides to fold or self-assemble into ordered structures (i.e., conformations with a higher level of secondary structure) when the temperature of the surrounding medium is raised. This increase in order with increased temperature is known as "inverse temperature transition" and the characteristic temperature at which the transition occurs for any given molecule is indicated by $T_1$. The structural change in the molecule is accompanied by contraction, i.e., heat energy is converted to movement. By virtue of these properties, the proteins have the ability to perform work.

The described structural changes do not necessarily require an increase in temperature. Other factors that induce secondary structural changes include the concentration of the polypeptide itself, changes in the level of ionization of amino acid side groups of the polypeptide which are effected by changes in the pH of the surrounding medium, the phosphorylation state of certain amino acid side chains, e.g., Ser, Thr, or Tyr, the redox state of physically associated prosthetic groups, and photochemical reactions of associated chromophores. Extrinsic factors that induce structural changes include changes in the concentration of salts and certain organic compounds present in the surrounding medium and changes in pressure.

For example, by decreasing the $T_1$ of an abductin biomaterial to below the body temperature of an organism, appropriate changes in the above factors result in an increase in its secondary structure and cause it to perform work. Alternatively, the temperature can be increased to effect a physico-chemical change in the abductin polypeptide or polymer. When the free energy input is effected by a change in the concentration of a chemical (e.g., sodium chloride) and the folding results in a contraction of the material, the process is referred to as "chemomechanical transduction," i.e., chemically-induced motion or work.

While the above-described properties of these polypeptides endow them with the ability to perform work, they do not render them elastic, i.e., resilient. For the polypeptides to be resilient, they need to be cross-linked. This resilience is due to a thermodynamically favored drive towards greater entropy. When the molecules are stretched, the degree of freedom is reduced and when the tension is released, the molecule reforms the contracted higher entropic contracted conformation. The above-described mechanisms of action are exemplary and it is emphasized that the present invention is not limited by a particular mechanism of action.

Abductin clones Ap4 and Ap7 have identical amino acid sequences (SEQ ID NO:6) (FIG. 2). The other three clones (Ap5, Ap9 and Ap12; SEQ ID NOS:7–9) differ slightly in length and amino acid sequence. The polypeptide sequences can be divided into two domains. The first domain (residues 1–20) is an Ala-rich N terminal domain. The first domain of each of clones Ap4, Ap7, Ap5 and Ap9 is identical (SEQ ID NO:11). In the fifth clone (Ap12) (SEQ ID NO:12), Val replaces Ala at position 14. The first domain contains two conserved Cys (residues 6 and 10) that may be involved in inter- or intramolecular disulfide formation; it also contains two of the three conserved Tyr (residues 4 and 20), which could also be involved in crosslinking by forming 3,3'-methylene bistyrosine. The first domain may form a signal sequence based on the observation that the agreement between the amino acid analysis of the inner hinge ligament and the composition predicted from the cDNA sequences is increased when the N-terminal residues are not included.

The second domain of each of clones Ap4 and Ap7 is identical (SEQ ID NO:13), whereas the second domain of clones Ap5, Ap9, and Ap12 (SEQ ID NOS:14–16) differs slightly in length and amino acid sequence. The second domains of the clones examined are extraordinarily Gly- and Met-rich and stretch from residue 21 to the C terminus. Methionines are distributed throughout this domain and are included in the consensus sequence Gly-Gly-Phe-Gly-Gly-Met-Gly-Gly-Gly-X (SEQ ID NO:10), which is found with the strongest compliance in the C-terminal half of the polypeptide. X can be any amino acid, e.g., Lys, Met, or Asn. The high glycine content is in keeping with an overall lack of secondary structure, and the conserved repeat sequences contribute to the properties described above to endow abductin with its mechanical properties. The overall sequence is extremely hydrophobic, especially since all the Asx and Glx residues in the clones examined were found to be Asn and Gln (FIG. 2). Further analysis indicated that the presence of methionine sulfoxide in place of methionine in the abductin sequence increases the polarity of the abductin polypeptide, the second domain is punctuated by Lys residues at positions 53 and 89, and the third conserved Lys is two residues from the C terminus. Finally, the third conserved Tyr is at the extreme C terminus. If the first domain is removed by a signal peptidase, these remaining Lys and Tyr residues are likely candidates for sites of crosslinking.

Abductin Polypeptides

The invention includes a functional polypeptide, abductin, and functional fragments thereof. The new hybrid abductin molecules contain various useful second components and functional fragments thereof. A "functional polypeptide" is a polypeptide that possesses a biological function or activity of naturally-occurring abductin. Functional polypeptides can be identified through assays described herein, e.g., those that measure elasticity or resilience. "Functional fragments" of the abductin polypeptide include, for example, fragments of abductin polypeptide that retain the activity of naturally occurring abductin polypeptide, e.g., the ability to increase the degree of secondary structure upon increase in temperature or high resilience. Smaller peptides, e.g., three amino acids to full-length abductin, endowing the biological activity of abductin are included in the invention. One of skill in the art can assay for functional activity of abductin by standard methods, e.g., by testing for an increase in secondary structure upon increasing the temperature or testing for resilience.

Minor modifications of the primary amino acid sequence of the full-length abductin polypeptide, the abductin repeat polymers containing one or more glycine-rich abductin-derived monomeric units and the hybrid abductin molecules can result in molecules with substantially equivalent activity, e.g., 50% of the elastic property of abductin, preferably 75%, more preferably 90, 95, or 99% of the elastic property of abductin compared to the naturally occurring abductin described herein. Such modifications may be deliberate, as by site-directed mutagenesis, or may be spontaneous. All of the polypeptides produced by these modifications are included herein provided that the biological activity of abductin polypeptide, e.g., high resilience (i.e., elasticity) is retained.

Furthermore, deletion of one or more amino acids can also result in a modification of the structure of the resultant molecule without significantly altering its activity. This can lead to the development of a smaller active molecule which would have broader utility. For example, it is possible to remove one or more, e.g., 5, 10, 20, 25, or 50 amino or carboxy terminal amino acids (or to remove amino acids at both the amino or carboxy termini) which may not be required for the polypeptide's activity. The resulting molecule can be tested for its ability to increase the order based upon secondary structure upon an increase in temperature, or for resilience after cross-linking by methods described herein.

In the case of new abductin polypeptides, abductin repeat polymers and hybrid abductin molecules which are less than 100% identical to a reference sequence, the non-identical positions are preferably, but not necessarily, conservative substitutions for the reference sequence. A "conservative substitution" is the replacement of an amino acid residue by another, chemically similar residue. Examples of conservative substitutions include the replacement of one hydrophobic residue such as isoleucine, valine, leucine or methionine with another, or the replacement of one polar residue for another, such as the substitution of arginine for lysine, glutamic for aspartic acids, or glutamine for asparagine, and the like. Preferably conservative substitutions do not significantly alter the structure or activity of the polypeptide, e.g., antibodies raised to the substituted polypeptide also immunoreact with the unsubstituted polypeptide. The resulting mutant forms have at least 50%, e.g., 60%, 75%, 85%, 95%, 99%, or 100% of the activity of the naturally occurring abductin protein, as measured by assays described herein.

Peptides and polypeptides of the invention can be obtained by a variety of means. Due to its insolubility in water and other solvents, e.g., urea and guanidinium isothiocyanate, abductin has not been purified from natural sources. Smaller peptides (less than 100 amino acids long) may be conveniently synthesized by standard chemical methods familiar to one of ordinary skill in the art, e.g., Creighton (1983) Proteins: Structures and Molecular Principles, W. H. Freeman and Co., N.Y.; and U.S. Pat. No. 5,336,256. These methods can also be used to insert non-natural or post-translationally modified amino acids, e.g., Hyp and DOPA.

Abductin polypeptides can be recombinantly or synthetically produced in the naturally-occurring full-length form, as a truncated protein, or as a fusion protein including two or more abductin polypeptides or an abductin polypeptide and a different polypeptide, e.g., fibroin. A chimeric polypeptide is a molecule in which different portions are derived from different proteins. For example, a chimeric protein may contain a domain of abductin and another domain of silk protein (fibroin). Methods of producing chimeric proteins involve splicing a portion of a gene encoding a given protein or fragment thereof to one or more proteins or fragments thereof derived from one or more genes encoding different proteins, and are known in the art.

Methods include, for example, in vitro recombinant DNA techniques, synthetic techniques, and in vivo genetic recombination. See, for example, the techniques described in Sambrook et al. (1989) Molecular Cloning, A Laboratory Manual, Cold Spring Harbor Press, N.Y.; and Ausubel et al., (cited supra). Alternatively, nucleic acids encoding the proteins may be chemically synthesized. See, for example, the techniques described in Oligonucleotide Synthesis, (1984) Gait, M. J. ed., IRL Press, Oxford.

A substantially pure synthetic abductin repeat polymer contains multiple copies of a glycine-rich abductin monomer unit. Such polymers can be polymers comprising two to five hundred monomer units. They will optimally contain more than ten and less than one hundred monomer units. The monomer units can contain from three consecutive amino acids of the abductin sequence up to the full length abductin sequence. The monomer units are preferably less than fifty, more preferably less than twenty five and most preferably less than twelve amino acids in length. For example, such a monomer unit can be the abductin repeat sequence Gly-Gly-Phe-Gly-Gly-Met-Gly-Gly-Gly-X (SEQ ID NO:10). Examples of other possible abductin repeat sequences that can be used as monomer units include Gly-Gly-X, Gly-Gly-Gly-X (SEQ ID NO:39), Gly-Gly-X-Gly-Gly-X (SEQ ID NO:40), Gly-Gly-Phe-Gly-Gly-Met-Gly-Gly-X (SEQ ID NO:41), Gly-Gly-X-Gly-Gly-Phe-Gly-Gly-Met (SEQ ID NO:42) and Gly-Gly-Gly-X-Gly-Gly-Phe-Gly-Gly-Ile-Gly-Gly-Phe-Gly-Gly-Met-Gly-Gly-Gly-X (SEQ ID NO:43). X can be any amino acid, preferably Lys, Met, Asn or Pro.

Other useful amino acids, for example, at position 10 of the repeat sequence of SEQ ID NO:10 can be identified by preparing abductin repeat polymers with different monomeric units consisting of this repeat sequence but containing different amino acids at position 10 and testing them for increases in secondary structure upon increase in temperature. Changes in secondary structure can be detected, for example, by circular dichroism (CD) (see Example 3). Alternatively, the resiliency (i.e., elastic modulus) of cross-linked material made from the abductin repeat polymer can be tested for by methods known to those of ordinary skill in the art using, for example, a stress-strain apparatus as described in U.S. Pat. No. 4,898,926. The degree of resiliency is determined by the application for which the relevant abductin repeat polymer is to be used.

The optimal number of copies of monomer units in a particular abductin repeat polymer can similarly be determined by preparing abductin repeat polymers of different lengths and testing them for temperature-dependent changes in secondary structure or by quantitating their resilience, as described herein. The degree of resiliency of a material can be further modulated by making mixed polymers using two or more abductin repeat units as a source of monomer units. For example, a first monomer unit to be used could be one that, on its own in a polymer, results in a high level of resiliency in that polymer; a second monomer unit could be one that on its own in a polymer results in no resiliency in the polymer. By altering the relative numbers of monomer units 1 and 2 in the polymer, it is possible to produce polymers with varying degrees of resiliency. For example, one monomer unit can be a peptide with a sequence of SEQ ID NO:10 where amino acid X is one amino acid and the second monomer unit can be a peptide with a sequence of SEQ. ID NO:10 where X is an amino acid other than that in the first monomer. When more than one monomer unit is used to produce an abductin repeat polymer, the additional monomer units (e.g., second, third, or fourth monomer units) can contain three to about one hundred amino acid residues. The abductin repeat polymers can be prepared chemically or by recombinant technology using methods known to artisans of ordinary skill.

Cross-Linking

For resilience, it is preferred to introduce artificial intermolecular cross-links into the abductin repeat polymers. This can be accomplished by a number of means known to those of ordinary skill in the art, for example, exposing the polymers to ionizing radiation (see, e.g., U.S. Pat. No. 4,474,851). In addition, amino acids of the peptide subunits can be chemically modified or substituted in order to form reactive side-groups that react with each other to form cross-links by, for example, amide linkages, disulfide linkages, Schiff base formation, ester formation or enzymatic cross-linking by lysyl oxidase. Photoactivatable agents such as those resulting in carbenes or nitrenes, attached as amino acid side groups can also be used to introduce crosslinks (see, e.g., U.S. Pat. No. 4,474,851).

To determine the effect of crosslinks and the optimal number of crosslinks per monomer unit, the resiliency of a crosslinked polymer can be measured using methods known in the art. The level of cross-linking can vary provided that the resulting abductin repeat polymer displays the requisite resilient properties. For example, when the cross-linking is by gamma-irradiation, the degree of cross-linking is a function of the time and energy of the irradiation. The time required to achieve a desired level of cross-linking may readily be computed by exposing non-cross-linked polymer to the source of radiation for different time intervals and determining the degree of resilience (elastic modulus) of the resulting cross-linked material for each time interval. By this experimentation, it will be possible to determine the irradiation time required to produce a level of resiliency appropriate for a particular application (see, e.g., U.S. Pat. No. 4,474,851). The abductin repeat polymers are preferably lightly crosslinked. The minimum number of cross-links is one for every two abductin polypeptides. Preferably, the extent of cross-linking is at least about one cross-link for every five or ten to one hundred monomer units, e.g., one cross-link for every twenty to fifty monomer units.

Hybrid Abductin Molecules

Substantially pure "hybrid abductin molecules" include an abductin polypeptide or an abductin repeat polymer (referred to herein as the "first" or "resilient" component) physically linked to another polymeric molecule, or a functional fragment thereof (referred to as the "second component"). These new molecules can have various desired functions and properties. The abductin polypeptides and abductin repeat polymers used for the production of these hybrid abductin molecules are the same as those described above. The abductin repeat polymers can optionally be cross-linked, depending on the application for which the relevant material is to be used.

It is important that the two components of a hybrid abductin molecule be linked by some form of chemical bond, for example a covalent bond, to prevent the two components from becoming separated when the resilient component is stretched or relaxed. Other types of appropriate chemical bonds include ionic bonds and hydrogen bonds or electrostatic interactions such as ion-dipole and dipole-dipole interactions. The linkage may be formed, for example, by the methods described above for cross-linking of the resilient component. It may be necessary to provide appropriate chemical moieties in the second component to allow cross-linking with the first, resilient component. Such moieties are well-known to skilled artisans and include, for example, amino, and carboxylic groups. Where the second component is a protein, the association between the components can be effected by recombinant nucleic acid technology.

A hybrid abductin molecule can contain various numbers of both components. For example they can contain (a) one molecule of each component, (b) one molecule of the first component and a plurality of molecules (e.g., two to five hundred or ten to one hundred) of the second component, (c) a plurality of molecules of the first component and one molecule of the second component, or (d) a plurality of molecules of both components. Optimal numbers and positioning of inserted sequences can be determined as described herein. The degree of linkage between the two components and the relative number of each component in the final hybrid abductin molecule can be varied so as to provide the desired level of the function of both components. The hybrid abductin molecules include those in which the fragments of second the components are inserted within the sequence of the abductin polypeptide. Alternatively, abductin repeat sequences can be inserted in the second component molecules. The inserted sequences can be inserted tandemly or alternately.

For example, to make biomaterials that require strength as well as resilience, a first component can be combined with a load-bearing second component. Examples of naturally occurring load-bearing polymers are collagen and silk or silk-like proteins, e.g., insect-derived silk proteins. Other suitable types of polymers that could used as second components to endow strength include polyamides, polyesters, polyvinyls, polyethylenes, polyurethanes, polyethers, and polyimides. Hybrid abductin molecules that include such polymers have a variety of uses including, for example, artificial joint ligaments where the second component is collagen (Takahara et al., *J. Biol. Chem.* 266:13124, 1991) or a functional fragment thereof. Functional fragments of collagen include those with the following sequence: Gly-Pro-Hyp, where Hyp is hydroxyproline.

Alternatively, by using silk worm, an insect or spider silk protein (e.g., fibroin) (Kikuchi et al., *Gene,* 110:151, 1992) or a functional fragment thereof (Guerette et al., *Science* 272:112, 1996), as the second component, an extremely light-weight, resilient, and durable thread or filament can be produced, which can be woven into a fabric. Such fabrics are useful in the manufacture, for example, of military clothing. Fragments of fibroin include those with the following sequences: Gly-Ala-Gly-Ala-Gly-Ser (SEQ ID NO:23), Ala-Ser-Ala-Ala-Ala-Ala-Ala-Ala (SEQ ID NO:24), Ser-Ser-Ala-Ala-Ala-Ala-Ala-Ala-Ala-Ala (SEQ ID NO:25), and Ala-Ala-Ala-Ala-Ala-Ala-Ala-Ala (SEQ ID NO:26). In both the above examples, the first component is cross-linked.

The new abductin repeat polymers can also be used to make hybrid polypeptides that are soluble at one temperature but that, at a another defined temperature ($T_1$), gain a significant degree of appropriate secondary structure and precipitate, i.e., become insoluble. An appropriate abductin consensus sequence polymer is linked to a second polypeptide to create a hybrid polypeptide containing a predetermined optimal molecular ratio of the two components. The abductin repeat polymers used will not be cross-linked.

In establishing the optimal design of an appropriate abductin hybrid polymer, it will be important that the temperature at which it becomes insoluble is below that at which it irreversibly denatures. For example, a hybrid polypeptide, in which the second component is an enzyme employed in large scale liquid phase conversion of a substrate to a useful product will provide a relatively simple method to recover the enzyme after completion of the reaction. Merely by heating the reaction mixture to the appropriate temperature ($T_1$), the hybrid enzyme-containing polypeptide is insolubilized and thereby rendered recoverable by relatively simple procedures involving differential sedimentation known to those of ordinary skill in the art, e.g., centrifugation. The hybrid polypeptides will subsequently be resolubilized, and thereby made reusable, by decreasing the temperature to below the established critical level.

Examples of useful enzymes include those used in the manufacture of pharmaceuticals such as beta-lactam-acylases (e.g., penicillin G acylases, penicillin V acylases and glutaryl-7-aminocephalosporonic acid acylases). Other suitable enzymes are lipases (e.g. *Candida rugosa* lipase), useful in the manufacture of, for example, pharmaceuticals, cosmetics, detergents, foods, perfumes, medical diagnostics, leather goods and other synthetic organic substances.

Previously described resilient biomaterials have been found to exhibit both low and high adhesiveness with respect to cells and biological polymers such as proteins and nucleic acids. The cell adhesiveness and resiliency of the abductin biomaterial can be altered as described above by changing the ratio of components of a copolymer and/or the amino acid composition of the repeat sequences within a polymer. Candidate materials can be tested for low cell (e.g., fibroblast or endothelial cell) adhesiveness by methods known in the art and described in detail in U.S. Pat. No. 5,527,610 which is incorporated herein by reference in its entirety. Where the abductin biomaterial is made from a hybrid abductin molecule, useful second components can be, for example, collagen or a functional fragment thereof. The resilient polypeptides used for this application will, in general, be lightly cross-linked.

A hybrid abductin molecule, which incorporates as a second component an adhesin polypeptide, e.g., mussel adhesin polypeptide derived from *Mytilus edulis, Mytilus californianus,* or *Geukensia demissa* (Ou, Ph.D. Thesis, Boston University, 1990, UMI Accession No: 9023770); Taylor et al., *J. Am. Chem. Soc.,* 116:10355 1994; Laursen, in Results and Problems in Cell Differentiation Biopolymers Ed. Case, E. T., Berlin Heidelberg, 1992), or functional fragments thereof, can be used as a biological or tissue glue. Tissue glues are useful, for example, as an alternative to surgical sutures. In this case, an abductin repeat polymer is designed such that the resulting hybrid abductin molecule is in a fluid form at temperatures below the body temperature of the subjects for which it is intended. However, at physiological body temperature, it sets.

Alternatively, the hybrid abductin can have a higher $T_1$, such that it requires exposure to an exogenous heat source to set. Abductin repeat polymers with varying degrees of adhesiveness can be made by altering the parameters described above, e.g., copolymer composition and amino acid sequences of the repeat sequences within a polymer; the resulting polymers can then be tested for adhesiveness using methods known in the art. Functional fragments of the mussel adhesins include those with the following sequences: Ala-Lys-Pro-Ser-Tyr-Hyp-Hyp-Thr-DOPA-Lys (SEQ ID NO:33), Arg-Lys-Pro-Ser-Tyr-Hyp-Hyp-Thr-DOPA-Lys (SEQ ID NO:34), Arg-Lys-Ile-Ser-Tyr-Hyp-Hyp-Thr-DOPA-Lys (SEQ ID NO:35), Arg-Lys-Thr-Ser-Tyr-Hyp-Hyp-Thr-DOPA-Lys (SEQ ID NO:36), Gly-Lys-Pro, Ala-Lys-Pro, Gly-Gln-Gln-Lys-Gln (SEQ ID NO:37), and Gly-Gly-Val-Gln-Lys (SEQ ID NO:38) where Hyp is hydroxyproline (trans-4-hydroxyproline, trans-3-hydroxyproline or trans-2,3-cis-3,4 -dihydroxyproline) and DOPA is (3,4-dihydroxyphenyl)-L-alanine (Taylor et al. cited supra; Laursen, cited supra).

The resilient polypeptides used making adhesive hybrid abductin molecules will, in general, be cross-linked. Hybrid abductin molecules with even greater resilience than abductin or an abductin repeat polymer can be produced by using as a second component an elastin polypeptide or a functional fragment thereof. Routine experimentation as described above can be used to determine the optimum amino acid composition of each component and the ratio of components for such hybrid abductin molecules.

The invention also features hybrid abductin molecules that include fibroin- or functional fragments thereof, but containing, in addition, an elastin polypeptide or a synthetic polymer composed of multiple copies of an elastin functional fragment (i.e., an elastin repeat unit). Elastin functional fragments include those with the following sequences: Val-Pro-Gly-Val-Gly (SEQ ID NO:27), Val-Pro-Ala-Val-Gly (SEQ ID NO:28) or Val-Pro-Gly-Gly (SEQ ID NO:29) [U.S. Pat. Nos. 4,589,882 and 4,783,523]. Other elastin sequences include X-Ile-Pro-Gly-Val-Gly-Z (SEQ ID NO:30), wherein X is Pro-Gly-Val-Gly (SEQ ID NO:31), Gly-Val-Gly, Val-Gly, Gly or a covalent bond and Z is Ile-Pro-Gly-Val (SEQ ID NO:32), Ile-Pro-Gly, Ile-Pro, Ile or a covalent bond (U.S. Pat. No. 4,783,523). These hybrid abductin molecules will preferably be cross-linked.

Uses of the Abductin Polypeptides

The new, cross-linked resilient abductin polypeptides and polymers and their un-cross-linked precursors exclude water upon exposure to an increase in temperature by assuming a more organized secondary structure, i.e., a temperature induced decrease in entropy. They can therefore be used in the manufacture of drug delivery vehicles to administer water soluble drugs. For example, the abductin drug delivery vehicles can be produced in the form of microspheres into which a drug is incorporated during manufacture. The material is designed such that the temperature at which it changes its secondary structure ($T_1$) is slightly below body temperature (e.g., 2° C., 3° C., or 5° C. below body temperature) such that on being introduced into the body of a subject (e.g., a human patient), it releases the water soluble drug into the surrounding tissue. Alternatively, the $T_1$ of the abductin molecule could be significantly above body temperature and an appropriate body part or region is exposed to an external heat source to induce drug release from the abductin drug delivery vehicle. Upon reaching the critical temperature, the abductin-containing material extrudes water containing the drug into the surrounding tissue. An exogenous heat source can therefore be used in conjunction with a drug-loaded abductin-containing biomaterial for tissue-targeted drug delivery. Such a mode of delivery is frequently desirable, especially where it is necessary to minimize systemic toxic effects of relevant drugs.

Routine experimentation analogous to that described above can be used to determine the optimum parameters to use in making an abductin drug delivery vehicle, e.g., the number of abductin repeat monomer units in the abductin repeat polymer. Administration of the drug/abductin vehicle composition can be local, i.e., directly to the organ or tissue of interest, parenteral, e.g., intravenous, intramuscular, intradermal, subcutaneous or intraperitoneal, or transmucosal, e.g., intranasal, intragastric, intrarectal, intravaginal or intratracheal. Where the administration is topical, the temperature increase required to trigger drug delivery to the skin can be effected by an exogenous light or heat source, e.g., a heat lamp.

The new materials (abductin polypeptides, abductin repeat polymers, and hybrid abductin molecules) that display (a) resilience compatible with relevant tissues, (b) biocompatibility, (c) biodegradability and/or (d) sterilizability together with low biological adhesiveness are useful for the manufacture of barriers for isolating wound repair sites from adhesions with neighboring tissues and other repair sites. Such repair sites can result from surgery or trauma. Biomaterials made of abductin polypeptides are also useful in the manufacture of tissue prostheses, e.g., joint ligament prostheses.

Incorporating cell adhesion sequences into the new resilient materials would result in a material useful for applications in which cell adhesiveness is desirable. For example, by inclusion of at least one copy of the fibronectin-derived Arg-Gly-Asp-X sequence (SEQ ID NO:22) (where X can be any amino acid, preferably Ser and Val) in a hybrid abductin molecule would result in a material with properties (a)–(d) recited above and, in addition, high cell adhesiveness. The Arg-Gly-Asp-X (SEQ ID NO:22) sequence has been shown to be the ligand epitope recognized by several cellular adhesion receptors of the integrin superfamily and are expressed on a broad range of cell types, e.g., fibroblasts and vascular endothelial cells.

Routine experimentation involving making abductin hybrid molecules containing different numbers of copies of this sequence and testing them for both the ability to increase secondary structure upon increase of temperature and for cell adhesiveness, will indicate the number of copies of the sequence to use in order to prepare an optimal product. Similar testing with the sequence of SEQ ID NO:22 containing different amino acid residues at position X will define amino acids to use at this position that result in a polypeptide that retains the abductin property of interest.

Devices to be made from such a material would be those in which it is desired that cells attach, grow, and remodel to form, for example, a natural tissue analog. Thus, such a material would be useful for certain tissue or organ prostheses, e.g., artificial joint cartilage or as an artificial intimal lining for vascular prostheses. Other substances, such as chemotactic, differentiative, and cell-growth factors or enzymes such as proteases or nucleases can be co-incorporated into such prostheses. These substances can be included by mixing them together with the other components during the formation of the device. The resilient polypeptides used for these devices will, in general, be lightly cross-linked.

The materials of the invention, i.e., purified naturally occurring abductin, abductin repeat polymers, or hybrid abductin molecules, can be manufactured in various useful physical forms, e.g., woven or nonwoven sheets, gels, foams, powders, or solutions. Furthermore, where desired, the materials, during manufacture, can be molded into appropriate shapes as, for example, in the case of medical prostheses such as vascular prostheses or joint prostheses.

When used in vivo, and in particular inside the body of a subject, e.g., a human patient, it is important that the material be biocompatible. A "biocompatible" material is not substantially mutagenic, antigenic, inflammatory, pyrogenic, or hemolytic. Furthermore, it must neither exhibit substantial cytotoxicity, acute systemic toxicity, or intracutaneous toxicity, nor significantly decrease clotting time. In vivo and in vitro tests for these undesirable biological activities are well known in the art; examples of such assays are given, for example, in U.S. Pat. No. 5,527,610. Also, when used in vivo, the materials may be biogradable.

In light of their high glycine content, insolubility, chemical inertness, structural similarity to certain endogenous mammalian (e.g., human) proteins (e.g., collagen and elastin), and biodegradability, the abductin polypeptides and the abductin-derived polymers and hybrid molecules used for in vivo applications (e.g., prostheses and tissue adhesion-preventing barriers) are likely to be substantially biocompatible. In the unlikely event that toxicity or immunogenicity, for example, occurs in a relevant material, methods for modulating these undesirable effects are known in the art. For example, "tanning" of the material by treating it with chemicals such as aldehydes (e.g., glutaraldehyde) or metaperiodate will substantially decrease both toxicity and immunogenicity. Preferably, the materials used to make devices for in vivo use are also sterilizable.

Nucleic Acid Molecules, Vectors, Expression Vectors and Transfected Cell Lines

A variety of host-expression vector systems can be used to express abductin polypeptides and other recombinant nucleotide sequences. Where the peptide or polypeptide is soluble, it can be recovered from: (a) the culture, i.e., from the host cell in cases where the peptide or polypeptide is not secreted; or (b) from the culture medium in cases where the peptide or polypeptide is secreted by the cells. The expression systems also encompass engineered host cells that express the polypeptide in situ, i.e., anchored in the cell membrane. Purification or enrichment of the polypeptide from such an expression system can be accomplished using appropriate detergents and lipid micelles and methods well known to those skilled in the art. Alternatively, such engineered host cells themselves can be used in situations where it is important not only to retain the structural and functional characteristics of the protein, but also to assess biological activity.

The expression systems that can be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleotide sequences; yeast transformed with recombinant yeast expression vectors; insect cells infected with recombinant viral expression vectors (baculovirus); plant cell systems infected with recombinant viral expression vectors (e.g., cauliflower mosaic virus, CaMV; tobacco mosaic virus, TMV) or transformed with recombinant plasmid expression vectors; or mammalian cells (e.g., COS, CHO, BHK, 293, 3T3) harboring recombinant expression constructs containing promoters derived from the genome of mammalian cells (e.g. metallothionein promoter) or from mammalian viruses.

In bacterial systems, a number of expression vectors may be advantageously selected depending upon the use intended for the gene product being expressed. For example, when a large quantity of such a protein is to be produced, e.g., for raising antibodies to the protein, vectors which direct the expression of high levels of fusion protein products that are readily purified may be desirable. Such vectors include, but are not limited to, the *E. coli* expression vector pUR278 (Ruther et al., *EMBO J.*, 2:1791, 1983), in which the coding sequence may be ligated individually into the vector in frame with the lacZ coding region so that a fusion protein is produced; pIN vectors (Inouye & Inouye, *Nucleic Acids Res.*, 13:3101, 1985; Van Heeke & Schuster, *J. Biol. Chem.*, 264:5503, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems can be utilized. In cases where an adenovirus is used as an expression vector, the nucleotide sequence of interest may be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (e.g., See Logan & Shenk, *Proc. Natl. Acad. Sci. USA*, 81:3655, 1984). Specific initiation signals may also be required for efficient translation of inserted nucleotide sequences. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (Bittner et al., *Methods in Enzymol.*, 153:516, 1987).

In addition, a host cell strain can be chosen which modulates the expression of the inserted sequences, or modifies and processes the gene product in the specific fashion desired. Such modifications (e.g., glycosylation and generation of Hyp and DOPA residues) and processing (e.g., cleavage) of protein products can be important for the function of the protein. Appropriate cell lines or host systems can be chosen to ensure the correct modification and processing of the foreign protein expressed. Mammalian host cells include but are not limited to CHO, VERO, BHK, HeLa, COS, MDCK, 293, 3T3, and WI38.

For long-term, high-yield production of recombinant proteins, stable expression is preferred. For example, cell lines which stably express the sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells can be allowed to grow for 1–2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the gene product. Such engineered cell lines can be particularly useful in screening and evaluation of compounds that affect the endogenous activity of the gene product.

A fusion protein can be readily purified by utilizing an antibody or a ligand that specifically binds to the fusion protein being expressed. For example, a system described by Janknecht et al., *Proc. Natl. Acad. Sci. USA*, 88:8972, 1991) allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers. If desired, the histidine tag can be selectively cleaved with an appropriate enzyme.

In addition, large quantities of recombinant polypeptides can advantageously be obtained using genetically modified organisms (e.g., plants or mammals), wherein the organisms harbor exogenously derived transgenes encoding the polypeptide of interest (Wright et al., *Bio/technology*, 5:830, 1991; Ebert et al., *Bio/technology*, 9:835, 1991; Velander et al., *Proc. Natl. Acad. Sci. USA*, 89:12003, 1993; Paleyanda et al., *Nature Biotechnology*, 15:971, 1997; Hennighausen, *Nature Biotechnology*, 15:945, 1997; Gibbs, *Scientific American*, 277:44, 1997). The polypeptide of interest is expressed in a bodily tissue and then is purified from relevant tissues or body fluids of the appropriate organism. For example, by directing expression of the transgene to the mammary gland, the protein is secreted in large amounts into the milk of the mammal from which it can be conveniently purified (e.g., Wright et al., cited supra, Paleyanda et al., cited supra; Hennighausen, cited supra).

Abductin-Specific Antibodies

Antibodies can be prepared that specifically recognize epitopes of the new abductin polypeptides, such as within the amino acid sequences of SEQ ID NOS:6, 7, 8, or 9. Such antibodies include, but are not limited to, polyclonal antibodies, monoclonal antibodies (mAbs), humanized or chimeric antibodies, single chain antibodies, Fab fragments, $F(ab')_2$ fragments, and epitope-binding fragments of any of the above.

The antibodies of the invention can be used, for example, in the purification of abductin polypeptides, abductin repeat polymers, and hybrid abductin molecules by methods known to those of ordinary skill in the art, e.g. affinity chromatography. The antibodies can also be used for testing for maintenance of native structure in abductin polypeptides in which amino acid replacements, additions, or deletions have been made. An additional use of these antibodies is as a component of a "follow-up" procedure for the detection of the polypeptides, abductin repeat polymers, or hybrid abductin molecules in bodily fluids (e.g., blood, plasma or serum) of subjects that had previously been contacted with a biomaterial containing one or more of these substances, e.g., human patients grafted with a prosthetic device made from one or more of the molecules.

For the production of antibodies of the invention, a host animal is immunized by injection with a polypeptide containing the amino acid sequence of SEQ ID NOS:6, 7, 8, or 9, a glycine-rich peptide fragment thereof, e.g., the consensus repeats peptide with the sequence of SEQ ID NO:10, or a polymer made using such peptides as monomer units. Host animals may include but are not limited to sheep, goats, horses, pigs, cows, rabbits, guinea pigs, mice and rats. Various adjuvants may be used to increase the immunological response, depending on the host species, including but not limited to Freund's (complete and incomplete) adjuvant, mineral gels such as aluminum hydroxide, lysolecithin, pluronic polyols, polyanions, peptides, oil emulsions, BCG (bacille Calmette-Guerin) and *Corynebacterium parvum*. Polyclonal antibodies are heterogeneous populations of antibody molecules derived from the sera of the immunized animals.

To further enhance immunogenicity, the immunogen may be coupled to a carrier. Examples of such carriers are keyhole limpet hemocyanin (KLH) and bovine serum albumin (BSA). Other albumins such as ovalbumin, mouse serum albumin or rabbit serum albumin can also be used as carriers. Methods of coupling a peptide to a carrier are well known in the art and include the use of glutaraldehyde, carbodiimide and m-maleimidobenzoyl-N-hydroxysuccinimide ester.

The amount of antigen to be used can be determined readily by those of average skill in the art without undue experimentation. The antigen can be administered by a number of routes (subcutaneous, intramuscular, intradermal, intravenous, intraperitoneal or transmucosal). The production of polyclonal antibodies is monitored by sampling blood of the immunized animal at various time points after administration. When the desired level of antibody is obtained, the animal is bled and the serum is stored.

Monoclonal antibodies (mAb), which are homogeneous populations of antibodies to a particular antigen, may be obtained by any technique which provides for the production of antibody molecules by continuous cell lines in culture. These include, but are not limited to, the hybridoma technique (Kohler and Milstein, *Nature*, 256:495–497, 1975; U.S. Pat. No. 4,376,110; Howell and Lane, *Antibodies, A Laboratory Manual*, Cold Spring Harbor Press, N.Y., 1988, the human B-cell hybridoma technique (Kosbor et al., *Immunology Today*, 4:72, 1983; Cole et al., *Proc. Natl. Acad. Sci. USA*, 80:2026, 1983), and the EBV-hybridoma technique (Cole et al., *Monoclonal Antibodies And Cancer Therapy*, Alan R. Liss, Inc., 1985). Such antibodies may be of any immunoglobulin class including IgG, IgM, IgE, IgA, IgD and any subclass thereof.

In addition, techniques developed for the production of "chimeric antibodies" can be used (Morrison et al., *Proc. Natl. Acad. Sci. USA*, 81:6851, 1984; Neuberger et al., *Nature*, 312:604, 1984; Takeda et al., *Nature*, 314:452, 1985). These involve splicing a portion of a gene encoding, for example, a mouse antibody of appropriate antigen specificity to a portion of a gene encoding a human antibody of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science*, 242:423, 1988; Huston et al., *Proc. Natl. Acad. Sci. USA*, 85:5879, 1988; and Ward et al., *Nature*, 334:544, 1989) can be adapted to produce single chain antibodies against the epitopes of SEQ ID NOS:6,7,8 or 9. Single chain antibodies are formed by linking the heavy and light chain fragments of the Fv region via an amino acid bridge, resulting in a single chain polypeptide. They are conveniently produced by recombinant DNA techniques.

Antibody fragments which recognize specific epitopes may be generated by known techniques. For example, such fragments include but are not limited to the F(ab')$_2$ fragments which can be produced by pepsin digestion of the antibody molecule, and the Fab fragments which can be generated by reducing the disulfide bridges of the F(ab')$_2$ fragments. Alternatively, Fab expression libraries may be constructed (Huse et al., *Science*, 246:1275, 1989) to allow rapid and easy identification of monoclonal Fab fragments with the desired specificity.

Methods for screening antibodies for binding specificity are well known. These include but are not restricted to testing for: (a) binding to a polypeptide containing the amino acid sequence of SEQ ID NOS:6, 7, 8, or 9 or a peptide derived from these sequences, e.g. the peptide with SEQ ID NO:10; (b) lack of binding to peptides and polypeptides lacking these sequences; and (c) inhibition of binding to intact abductin polypeptides, abductin repeat polymers and hybrid abductin molecules by peptides derived from the polypeptide with the amino acid sequence of SEQ ID NOS:6, 7, 8, or 9, e.g., the peptide with the sequence of SEQ ID NO:10.

EXAMPLES

The following examples are meant to illustrate the invention and not to limit it.

Example 1

Cloning of Abductin Genes

Freshly dissected inner hinge ligaments from adult Argopecten animals were ground in 1.0 M aqueous acetic acid to extract traces of calcium carbonate. The insoluble residue was dried and subjected to amino acid analysis, which revealed an unusual composition rich in glycine (57.3% of residues) and with a high level of methionine (14.3% of residues). The extracted tissue was also digested with 15% (w/v) cyanogen bromide (CNBr) in 70% formic acid at room temperature for up to 48 hours or with 0.1 N HCl at 95° C. for 3 hour. The released peptides were separated by reverse-phase HPLC and subjected to automated Edman degradation and matrix-assisted laser-desorption ionization mass spectrometry (MALDI-MS) (Table 1).

TABLE 1

Edman Peptides from Argopecten Hinge Ligaments

| Peptide | Method | Sequence |
| --- | --- | --- |
| 26 | CNBr | NAGGFGGIGG (SEQ ID NO:17) |
| 27 | CNBr | GGGPGGFGGIGGGSGGFGG(M) (SEQ ID NO:18) |
| 70 | CNBr | GGGLGGFGGIGGFGG(M) (SEQ ID NO:19) |
| 11 | 0.1 N HCl | GFGG (SEQ ID NO:20) |
| 56 | 0.1 N HCl | GFGGMGG (SEQ ID NO:21) |

(M): homoserine lactone as determined by MALDI-MS

Degenerate primers based on the peptide sequences were used to amplify Argopecten genomic DNA. Two PCR products, ApG1 and ApG17 were used to screen an Argopecten oligo(dT)-primed cDNA library made from young animals (3 to 8 mm) in which the ligament is growing rapidly. Five full length cDNAs were obtained (Ap4, 5, 7, 9, and 12). The 136-amino-acid open reading frames of Ap4 and Ap7 (SEQ ID NO: 1 and 2) differ by one nucleotide at position 279, while the other three (SEQ ID NOS:3–5) were very closely related and could represent abductin gene family members or alleles from the population used to construct the library (FIG. 1). The deduced abductin amino acid sequences (SEQ ID NOS:6–9) contain the Edman sequences (FIG. 2), with the exception of peptide 70, which gave a single mismatch.

Example 2

Analysis of Abductin Gene Expression in Argopecten Organisms at Different Stages of Development The analysis of abductin transcripts by Northern blotting and RNase protection experiments showed that they are present only in the mantle tissue. RNase protection experiments were carried out on RNA from Argopecten eggs, and various larval stages through young adults at day 35 (Sastry, *Bull. Mar. Sci.*, 15:417, 1965). Weak transcription was first detected at day 15 (prodissoconch, stage 20, 0.19 mm) and a strong signal was seen at day 35 (preadult scallop, stage 25, 1.67 mm). Expression continued in the adult.

Example 3

Increase in the Secondary Structure of an Abductin Repeat Polymer with Increase in Temperature A solution of the abductin repeat polymer with the sequence (Gly-Gly-Phe-Gly-Gly-Met-Gly-Gly-Gly-Lys; SEQ ID NO:10)$_3$ was subjected to sequential increases in temperature over the range of 25° C. to 85° C. At each temperature CD spectra were recorded on an AVIV 62DS CD spectropolarimeter with a variable temperature control. The resulting spectra cannot be interpreted in terms of a conventional secondary structure of alpha helix, beta sheet, and turns. The strong signal obtained indicates the presence of significant secondary structure that assumes a higher level with increase in temperature. This is indicative of an entropy-driven folding process characteristic of components of resilient (elastic) materials.

These data indicate that a change in temperature induces physical and/or chemical changes in a polypeptide containing one or more copies of glycine-rich consensus repeat sequence of abductin. Other factors, e.g., pressure or pH, will, indirectly, have the same effect on such polypeptides. This property of a glycine-rich repeat sequence-containing polymer can be used as described above for, e.g., drug delivery and enzyme-mediated industrial processes such as antibiotic manufacture. Upon cross-linking, the molecules become resilient and, as such, are useful for other applications such as resilient fabrics and tissue prostheses.

Other Embodiments

Although the invention has been described with reference to the presently preferred embodiment, it should be understood that various modifications can be made without departing from the spirit of the invention. Other embodiments are within the following claims.

What we claim is:

1. A substantially pure nucleic acid molecule comprising a nucleotide sequence encoding an abductin polypeptide, wherein the sequence of said nucleic acid molecule is at least 75% identical to a sequence selected from the group consisting of SEQ ID NO:1, SEQ ID NO:2, SEQ ID NO:3, SEQ ID NO:4, and SEQ ID NO:5 and wherein said abductin polypeptide is capable of chemomechanical transduction or inverse temperature transition.

2. The nucleic acid molecule of claim 1, wherein the sequence is selected from the group consisting of SEQ ID NO:1, SEQ ID NO:2, SEQ ID NO:3, SEQ ID NO:4, and SEQ ID NO:5.

3. A substantially pure nucleic acid molecule comprising a sequence that hybridizes under stringent conditions to a nucleic acid molecule having a sequence selected from the group consisting of SEQ ID NO:1, SEQ ID NO:2, SEQ ID NO:3, SEQ ID NO:4, and SEQ ID NO:5, or a complement of any one of said sequences.

4. The substantially pure nucleic acid molecule of claim 1, comprising a sequence that encodes the amino acid sequence of any one of SEQ ID NOS:6, 7, 8, or 9.

5. A vector comprising the nucleic acid molecule of claim 1.

6. The nucleic molecule of claim 1, wherein said sequence is operably linked to a regulatory sequence for expression of said polypeptide, said regulatory sequence comprising a promoter.

7. A cell comprising the nucleic molecule of claim 6.

8. The nucleic acid molecule of claim 1, wherein the sequence of said molecule is at least 75% identical to SEQ ID NO:1.

9. The nucleic acid molecule of claim 1, wherein the sequence of said molecule is at least 75% identical to SEQ ID NO:2.

10. The nucleic acid molecule of claim 1, wherein the sequence of said molecule is at least 75% identical to SEQ ID NO:3.

11. The nucleic acid molecule of claim 1, wherein the sequence of said molecule is at least 75% identical to SEQ ID NO:4.

12. The nucleic acid molecule of claim 1, wherein the sequence of said molecule is at least 75% identical to SEQ ID NO:5.

13. The nucleic acid molecule of claim 1, wherein the sequence of said molecule is at least 95% identical to SEQ ID NO:1.

14. The nucleic acid molecule of claim 1, wherein the sequence of said molecule is at least 95% identical to SEQ ID NO:2.

15. The nucleic acid molecule of claim 1, wherein the sequence of said molecule is at least 95% identical to SEQ ID NO:3.

16. The nucleic acid molecule of claim 1, wherein the sequence of said molecule is at least 95% identical to SEQ ID NO:4.

17. The nucleic acid molecule of claim 1, wherein the sequence of said molecule is at least 95% identical to SEQ ID NO:5.

18. The nucleic acid molecule of claim 2, wherein the sequence of said molecule comprises SEQ ID NO:1.

19. The nucleic acid molecule of claim 2, wherein the sequence of said molecule comprises SEQ ID NO:2.

20. The nucleic acid molecule of claim 2, wherein the sequence of said molecule comprises SEQ ID NO:3.

21. The nucleic acid molecule of claim 2, wherein the sequence of said molecule comprises SEQ ID NO:4.

22. The nucleic acid molecule of claim 2, wherein the sequence of said molecule comprises SEQ ID NO:5.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
       (A) LENGTH: 411 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: Coding Sequence
       (B) LOCATION: 1...408
       (D) OTHER INFORMATION: The amino acid translation for SEQ ID
           Nos. 1 and 2 are identical and thus is presented only
           once (see SEQ ID No. 6.)

(xi) SEQUENCE DESCRIPTION: SEQ ID NO:1:

```
ATG AAC GCC TAC ATC TGT CTT GCT GCT TGT CTG ATC GCT GCT GTC AGC      48
Met Asn Ala Tyr Ile Cys Leu Ala Ala Cys Leu Ile Ala Ala Val Ser
 1               5                  10                  15

GCC GCC GGA TAC GGA GGC GGT GCC GGA AGT ATG GGC GGT ACC GGA GGA      96
Ala Ala Gly Tyr Gly Gly Gly Ala Gly Ser Met Gly Gly Thr Gly Gly
                20                  25                  30

ATG GGA GGC GGA ATG AAC GCA GGC GGA TTC GGC GGT ATG GGC GGA GGA     144
Met Gly Gly Gly Met Asn Ala Gly Gly Phe Gly Gly Met Gly Gly Gly
            35                  40                  45
```

```
ATG GGC GGA GGT AAA GGC GGA TTC GGC GGA ATA GGC GGA TTC GGC GGC      192
Met Gly Gly Gly Lys Gly Gly Phe Gly Gly Ile Gly Gly Phe Gly Gly
        50              55              60

ATG GGA GGT GGA ATG GGT GGA GGT CCA GGC GGA TTC GGT GGA ATG GGA      240
Met Gly Gly Gly Met Gly Gly Gly Pro Gly Gly Phe Gly Gly Met Gly
 65              70              75              80

GGT TTC GGC GGA ATG GGC GGC GGG AAA GGT GGA TTC GGA GGA ATG GGC      288
Gly Phe Gly Gly Met Gly Gly Gly Lys Gly Gly Phe Gly Gly Met Gly
            85              90              95

AGT GGT ATG GGA GGT TTC GGA GGA ATG GGA GGC GGA AAT GCC GGT TTC      336
Ser Gly Met Gly Gly Phe Gly Gly Met Gly Gly Gly Asn Ala Gly Phe
            100             105             110

GGC GGA ATG GGA GGC GGC AAT GCC GGA TTC GGT GGA ATG GGC GGC CAA      384
Gly Gly Met Gly Gly Gly Asn Ala Gly Phe Gly Gly Met Gly Gly Gln
            115             120             125

GGT GGA TTT GGC GGA AAA GGC TAT TAA                                  411
Gly Gly Phe Gly Gly Lys Gly Tyr
            130             135

(2) INFORMATION FOR SEQ ID NO:2:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...408
        (D) OTHER INFORMATION: The amino acid translation for SEQ ID
            Nos. 1 and 2 are identical and thus is presented only
            once (see SEQ ID No. 6.)

(xi) SEQUENCE DESCRIPTION: SEQ ID NO:2:

ATG AAC GCC TAC ATC TGT CTT GCT GCT TGT CTG ATC GCT GCT GTC AGC       48
Met Asn Ala Tyr Ile Cys Leu Ala Ala Cys Leu Ile Ala Ala Val Ser
 1               5                  10                  15

GCC GCC GGA TAC GGA GGC GGT GCC GGA AGT ATG GGC GGT ACC GGA GGA       96
Ala Ala Gly Tyr Gly Gly Gly Ala Gly Ser Met Gly Gly Thr Gly Gly
            20              25              30

ATG GGA GGC GGA ATG AAC GCA GGC GGA TTC GGC GGT ATG GGC GGA GGA      144
Met Gly Gly Gly Met Asn Ala Gly Gly Phe Gly Gly Met Gly Gly Gly
            35              40              45

ATG GGC GGA GGT AAA GGC GGA TTC GGC GGA ATA GGC GGA TTC GGC GGC      192
Met Gly Gly Gly Lys Gly Gly Phe Gly Gly Ile Gly Gly Phe Gly Gly
        50              55              60

ATG GGA GGT GGA ATG GGT GGA GGT CCA GGC GGA TTC GGT GGA ATG GGA      240
Met Gly Gly Gly Met Gly Gly Gly Pro Gly Gly Phe Gly Gly Met Gly
 65              70              75              80

GGT TTC GGC GGA ATG GGC GGC GGG AAA GGT GGA TTC GGG GGA ATG GGC      288
Gly Phe Gly Gly Met Gly Gly Gly Lys Gly Gly Phe Gly Gly Met Gly
            85              90              95

AGT GGT ATG GGA GGT TTC GGA GGA ATG GGA GGC GGA AAT GCC GGT TTC      336
Ser Gly Met Gly Gly Phe Gly Gly Met Gly Gly Gly Asn Ala Gly Phe
            100             105             110

GGC GGA ATG GGA GGC GGC AAT GCC GGA TTC GGT GGA ATG GGC GGC CAA      384
Gly Gly Met Gly Gly Gly Asn Ala Gly Phe Gly Gly Met Gly Gly Gln
            115             120             125

GGT GGA TTT GGC GGA AAA GGC TAT TAA                                  411
Gly Gly Phe Gly Gly Lys Gly Tyr
            130             135
```

(2) INFORMATION FOR SEQ ID NO:3:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...378

(xi) SEQUENCE DESCRIPTION: SEQ ID NO:3:

```
ATG AAC GCC TAC ATC TGT CTT TCT GCT TGT CTT ATC GCT GCT GTC AGC        48
Met Asn Ala Tyr Ile Cys Leu Ser Ala Cys Leu Ile Ala Ala Val Ser
 1               5                  10                  15

GCC GCC GGA TAC GGA GGT GGT GCC GGA AGT ATG GGC GGT ACC GGA GGA        96
Ala Ala Gly Tyr Gly Gly Gly Ala Gly Ser Met Gly Gly Thr Gly Gly
                20                  25                  30

ATG GGA GGC GGA ATG AAC GCA GGC GGA TTC GGC GGT ATG GGC GGA GGA       144
Met Gly Gly Gly Met Asn Ala Gly Gly Phe Gly Gly Met Gly Gly Gly
         35                  40                  45

ATG GGC GGA GGT AAA GGC GGA TTC GGC GGA ATG GGC GGA TTC GGC GGC       192
Met Gly Gly Gly Lys Gly Gly Phe Gly Gly Met Gly Gly Phe Gly Gly
     50                  55                  60

ATG GGA GGT GGA ATG GGC GGA GGT CCA GGC GGA TTC GGT GGA ATG GGA       240
Met Gly Gly Gly Met Gly Gly Gly Pro Gly Gly Phe Gly Gly Met Gly
 65                  70                  75                  80

GGT TTC GGA GGA ATG GGT GGC GGA AAA GGT GGA TTC GGA GGA ATG GGC       288
Gly Phe Gly Gly Met Gly Gly Gly Lys Gly Gly Phe Gly Gly Met Gly
                 85                  90                  95

AGT GGT ATG GGA GGT TTC GGA GGA ATG GGA GGC GGA AAT GCC GGT TTC       336
Ser Gly Met Gly Gly Phe Gly Gly Met Gly Gly Gly Asn Ala Gly Phe
                100                 105                 110

GGT GGA ATG GGC GGC CAA GGT GGA TTT GGC GGA AAA GGT TAT TAA           381
Gly Gly Met Gly Gly Gln Gly Gly Phe Gly Gly Lys Gly Tyr
         115                 120                 125
```

(2) INFORMATION FOR SEQ ID NO:4:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...393

(xi) SEQUENCE DESCRIPTION: SEQ ID NO:4:

```
ATG AAC GCC TAC ATC TGT CTT GCT GCT TGT CTG ATC GCT GCT GTC AGC        48
Met Asn Ala Tyr Ile Cys Leu Ala Ala Cys Leu Ile Ala Ala Val Ser
 1               5                  10                  15

GCC GCC GGA TAC GGA GGC GGT GCC GGA AGT ATG GGC GGT ACC GGA GGA        96
Ala Ala Gly Tyr Gly Gly Gly Ala Gly Ser Met Gly Gly Thr Gly Gly
                20                  25                  30

ATG GGA GGC GGA ATG AAC GCA GGC GGA TTC GGC GGT ATG GGC GGA ATG       144
Met Gly Gly Gly Met Asn Ala Gly Gly Phe Gly Gly Met Gly Gly Met
         35                  40                  45
```

```
GGC GGA GGT AAA GGC GGA TTC GGC GGA ATA GGC GGC TTC GGA GGT GGT     192
Gly Gly Gly Lys Gly Gly Phe Gly Gly Ile Gly Gly Phe Gly Gly Gly
         50                  55                  60

ATG GGT GGA GGT CCA GGC GGA TTC GGT GGA ATG GGA GGT TTC GGC GGA     240
Met Gly Gly Gly Pro Gly Gly Phe Gly Gly Met Gly Gly Phe Gly Gly
 65                  70                  75                  80

ATG GCG GCG AAA GGT GGA TTC GGA GGA ATG GGC AGT GGT ATG GGA GGT     288
Met Ala Ala Lys Gly Gly Phe Gly Gly Met Gly Ser Gly Met Gly Gly
                 85                  90                  95

TTC GGA GGA ATG GGA GGC GGA AAT GCC GGT TTC GGC GGA ATG GGA GGC     336
Phe Gly Gly Met Gly Gly Gly Asn Ala Gly Phe Gly Gly Met Gly Gly
            100                 105                 110

GGC AAT GCC GGA TTC GGT GGA ATG GGC GGC CAA GGT GGA TTT GGC GGA     384
Gly Asn Ala Gly Phe Gly Gly Met Gly Gly Gln Gly Gly Phe Gly Gly
        115                 120                 125

AAA GGC TAT TAA                                                     396
Lys Gly Tyr
    130

(2) INFORMATION FOR SEQ ID NO:5:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...396

(xi) SEQUENCE DESCRIPTION: SEQ ID NO:5:

ATG AAC GCC TAC ATC TGC CTT GCT GCT TGT CTT ATT GCT GTA GTC AGT      48
Met Asn Ala Tyr Ile Cys Leu Ala Ala Cys Leu Ile Ala Val Val Ser
  1               5                  10                  15

GCC GCC GGA TAC GGA GGC GGT GCC GGA AGT ATG GGC GGT ACC GGC GGA      96
Ala Ala Gly Tyr Gly Gly Gly Ala Gly Ser Met Gly Gly Thr Gly Gly
             20                  25                  30

ATG GGA GGT GGA ATG AAC GCA GGC GGA TTC GGC GGT ATT GGC GGA GGA     144
Met Gly Gly Gly Met Asn Ala Gly Gly Phe Gly Gly Ile Gly Gly Gly
         35                  40                  45

ATG GGC GGA GGT AAA GGA GGA TTC GGC GGA ATG GGC GGA GGT CCA GGT     192
Met Gly Gly Gly Lys Gly Gly Phe Gly Gly Met Gly Gly Gly Pro Gly
     50                  55                  60

GGA TTC GGC GGA ATT GGC GGA GGT TCA GGT GGA TTC GGT GGA ATG GGA     240
Gly Phe Gly Gly Ile Gly Gly Gly Ser Gly Gly Phe Gly Gly Met Gly
 65                  70                  75                  80

GGT TTC GGC GGA ATG GGC GGC GGA AAA GGT GGA TTC GGA GGA ATG GGC     288
Gly Phe Gly Gly Met Gly Gly Gly Lys Gly Gly Phe Gly Gly Met Gly
                 85                  90                  95

AGT AGC ATG GGA GGT TTC GGA GGA ATG GGA GGC GGA AAT GCC GGT TTC     336
Ser Ser Met Gly Gly Phe Gly Gly Met Gly Gly Gly Asn Ala Gly Phe
            100                 105                 110

GGT GGA ATG GGC GGT CAA AGT GGA ATG GGC GGT CAA AGT GGA TTT GGC     384
Gly Gly Met Gly Gly Gln Ser Gly Met Gly Gly Gln Ser Gly Phe Gly
        115                 120                 125

GGC AAA GGT TAT TAA                                                 399
Gly Lys Gly Tyr
        130
```

(2) INFORMATION FOR SEQ ID NO:6:

(i) SEQUENCE CHARACTERISTICS:
        (A) LENGTH: 136 amino acids
        (B) TYPE: amino acid
        (D) TOPOLOGY: linear (ii) MOLECULE TYPE: protein (v) FRAGMENT TYPE: internal (ix) FEATURE:
        (D) OTHER INFORMATION: This translation is for SEQ ID NOs:
            1 & 2.

(xi) SEQUENCE DESCRIPTION: SEQ ID NO:6:

```
Met Asn Ala Tyr Ile Cys Leu Ala Ala Cys Leu Ile Ala Val Ser
 1               5                  10                  15

Ala Ala Gly Tyr Gly Gly Gly Ala Gly Ser Met Gly Gly Thr Gly Gly
                20                  25                  30

Met Gly Gly Gly Met Asn Ala Gly Gly Phe Gly Gly Met Gly Gly Gly
             35                  40                  45

Met Gly Gly Gly Lys Gly Gly Phe Gly Gly Ile Gly Gly Phe Gly Gly
             50                  55                  60

Met Gly Gly Gly Met Gly Gly Gly Pro Gly Gly Phe Gly Gly Met Gly
 65                  70                  75                  80

Gly Phe Gly Gly Met Gly Gly Gly Lys Gly Gly Phe Gly Gly Met Gly
                 85                  90                  95

Ser Gly Met Gly Gly Phe Gly Gly Met Gly Gly Gly Asn Ala Gly Phe
                100                 105                 110

Gly Gly Met Gly Gly Gly Asn Ala Gly Phe Gly Gly Met Gly Gly Gln
            115                 120                 125

Gly Gly Phe Gly Gly Lys Gly Tyr
            130             135
```

(2) INFORMATION FOR SEQ ID NO:7:

(i) SEQUENCE CHARACTERISTICS:
        (A) LENGTH: 126 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:7:

```
Met Asn Ala Tyr Ile Cys Leu Ser Ala Cys Leu Ile Ala Val Ser
 1               5                  10                  15

Ala Ala Gly Tyr Gly Gly Gly Ala Gly Ser Met Gly Gly Thr Gly Gly
                20                  25                  30

Met Gly Gly Gly Met Asn Ala Gly Gly Phe Gly Gly Met Gly Gly Gly
             35                  40                  45

Met Gly Gly Gly Lys Gly Gly Phe Gly Gly Met Gly Gly Phe Gly Gly
             50                  55                  60

Met Gly Gly Gly Met Gly Gly Gly Pro Gly Gly Phe Gly Gly Met Gly
 65                  70                  75                  80

Gly Phe Gly Gly Met Gly Gly Gly Lys Gly Gly Phe Gly Gly Met Gly
                 85                  90                  95

Ser Gly Met Gly Gly Phe Gly Gly Met Gly Gly Gly Asn Ala Gly Phe
                100                 105                 110
```

```
Gly Gly Met Gly Gly Gln Gly Gly Phe Gly Gly Lys Gly Tyr
        115                 120                 125
```

(2) INFORMATION FOR SEQ ID NO:8:

(i) SEQUENCE CHARACTERISTICS:
        (A) LENGTH: 131 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:8:

```
Met Asn Ala Tyr Ile Cys Leu Ala Ala Cys Leu Ile Ala Val Ser
 1               5                  10                  15

Ala Ala Gly Tyr Gly Gly Gly Ala Gly Ser Met Gly Gly Thr Gly Gly
                20                  25                  30

Met Gly Gly Gly Met Asn Ala Gly Gly Phe Gly Gly Met Gly Gly Met
            35                  40                  45

Gly Gly Gly Lys Gly Gly Phe Gly Gly Ile Gly Gly Phe Gly Gly Gly
    50                  55                  60

Met Gly Gly Gly Pro Gly Gly Phe Gly Gly Met Gly Gly Phe Gly Gly
65                  70                  75                  80

Met Ala Ala Lys Gly Gly Phe Gly Gly Met Gly Ser Gly Met Gly Gly
                85                  90                  95

Phe Gly Gly Met Gly Gly Gly Asn Ala Gly Phe Gly Gly Met Gly Gly
                100                 105                 110

Gly Asn Ala Gly Phe Gly Gly Met Gly Gly Gln Gly Gly Phe Gly Gly
            115                 120                 125

Lys Gly Tyr
        130
```

(2) INFORMATION FOR SEQ ID NO:9:

(i) SEQUENCE CHARACTERISTICS:
        (A) LENGTH: 132 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:9:

```
Met Asn Ala Tyr Ile Cys Leu Ala Ala Cys Leu Ile Ala Val Val Ser
 1               5                  10                  15

Ala Ala Gly Tyr Gly Gly Gly Ala Gly Ser Met Gly Gly Thr Gly Gly
                20                  25                  30

Met Gly Gly Gly Met Asn Ala Gly Gly Phe Gly Gly Ile Gly Gly Gly
            35                  40                  45

Met Gly Gly Gly Lys Gly Gly Phe Gly Gly Met Gly Gly Pro Gly
    50                  55                  60

Gly Phe Gly Gly Ile Gly Gly Gly Ser Gly Gly Phe Gly Gly Met Gly
65                  70                  75                  80

Gly Phe Gly Gly Met Gly Gly Gly Lys Gly Gly Phe Gly Gly Met Gly
                85                  90                  95

Ser Ser Met Gly Gly Phe Gly Gly Met Gly Gly Gly Asn Ala Gly Phe
                100                 105                 110
```

```
Gly Gly Met Gly Gly Gln Ser Gly Met Gly Gly Gln Ser Gly Phe Gly
        115                 120                 125
Gly Lys Gly Tyr
        130
```

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (B) LOCATION: 10...10
        (D) OTHER INFORMATION: Xaa = any amino acid (xi) SEQUENCE DESCRIPTION: SEQ ID NO:10:

```
Gly Gly Phe Gly Gly Met Gly Gly Gly Xaa
 1               5                  10
```

(2) INFORMATION FOR SEQ ID NO:11:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:11:

```
Met Asn Ala Tyr Ile Cys Leu Ala Ala Cys Leu Ile Ala Ala Val Ser
 1               5                  10                  15
Ala Ala Gly Tyr
            20
```

(2) INFORMATION FOR SEQ ID NO:12:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:12:

```
Met Asn Ala Tyr Ile Cys Leu Ala Ala Cys Leu Ile Ala Val Val Ser
 1               5                  10                  15
Ala Ala Gly Tyr
            20
```

(2) INFORMATION FOR SEQ ID NO:13:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:13:

```
Gly Gly Gly Ala Gly Ser Met Gly Gly Thr Gly Gly Met Gly Gly Gly
 1               5                  10                  15
Met Asn Ala Gly Gly Phe Gly Gly Met Gly Gly Met Gly Gly Gly
            20                  25                  30
```

```
Lys Gly Gly Phe Gly Gly Ile Gly Gly Phe Gly Gly Met Gly Gly Gly
             35                  40                  45

Met Gly Gly Gly Pro Gly Gly Phe Gly Gly Met Gly Gly Phe Gly Gly
         50                  55                  60

Met Gly Gly Gly Lys Gly Gly Phe Gly Gly Met Gly Ser Gly Met Gly
 65                  70                  75                  80

Gly Phe Gly Gly Met Gly Gly Gly Asn Ala Gly Phe Gly Gly Met Gly
                 85                  90                  95

Gly Gly Asn Ala Gly Phe Gly Gly Met Gly Gly Gln Gly Gly Phe Gly
             100                 105                 110

Gly Lys Gly Tyr
         115
```

(2) INFORMATION FOR SEQ ID NO:14:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:14:

```
Gly Gly Gly Ala Gly Ser Met Gly Gly Thr Gly Gly Met Gly Gly Gly
 1               5                  10                  15

Met Asn Ala Gly Gly Phe Gly Gly Met Gly Gly Met Gly Gly Gly
             20                  25                  30

Lys Gly Gly Phe Gly Gly Met Gly Gly Phe Gly Gly Met Gly Gly Gly
             35                  40                  45

Met Gly Gly Pro Gly Gly Phe Gly Gly Met Gly Gly Phe Gly Gly
         50                  55                  60

Met Gly Gly Gly Lys Gly Gly Phe Gly Gly Met Gly Ser Gly Met Gly
 65                  70                  75                  80

Gly Phe Gly Gly Met Gly Gly Gly Asn Ala Gly Phe Gly Gly Met Gly
                 85                  90                  95

Gly Gln Gly Gly Phe Gly Gly Lys Gly Tyr
             100                 105
```

(2) INFORMATION FOR SEQ ID NO:15:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:15:

```
Gly Gly Gly Ala Gly Ser Met Gly Gly Thr Gly Gly Met Gly Gly Gly
 1               5                  10                  15

Met Asn Ala Gly Gly Phe Gly Gly Met Gly Met Gly Gly Gly Lys
             20                  25                  30

Gly Gly Phe Gly Gly Ile Gly Gly Phe Gly Gly Met Gly Gly Gly
         35                  40                  45

Pro Gly Gly Phe Gly Gly Met Gly Gly Phe Gly Gly Met Ala Ala Lys
         50                  55                  60

Gly Gly Phe Gly Gly Met Gly Ser Gly Met Gly Gly Phe Gly Gly Met
 65                  70                  75                  80

Gly Gly Gly Asn Ala Gly Phe Gly Gly Met Gly Gly Gly Asn Ala Gly
```

-continued

```
                 85                  90                  95
Phe Gly Gly Met Gly Gly Gln Gly Gly Phe Gly Gly Lys Gly Tyr
                100                 105                 110

(2) INFORMATION FOR SEQ ID NO:16:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:16:

Gly Gly Gly Ala Gly Ser Met Gly Gly Thr Gly Gly Met Gly Gly Gly
  1               5                  10                  15

Met Asn Ala Gly Gly Phe Gly Gly Ile Gly Gly Met Gly Gly Gly
                 20                  25                  30

Lys Gly Gly Phe Gly Gly Met Gly Gly Gly Pro Gly Gly Phe Gly Gly
                 35                  40                  45

Ile Gly Gly Gly Ser Gly Gly Phe Gly Gly Met Gly Gly Phe Gly Gly
                 50                  55                  60

Met Gly Gly Gly Lys Gly Gly Phe Gly Gly Met Gly Ser Ser Met Gly
 65                  70                  75                  80

Gly Phe Gly Gly Met Gly Gly Gly Asn Ala Gly Phe Gly Gly Met Gly
                 85                  90                  95

Gly Gln Ser Gly Met Gly Gly Gln Ser Gly Phe Gly Gly Lys Gly Tyr
                100                 105                 110

(2) INFORMATION FOR SEQ ID NO:17:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:17:

Asn Ala Gly Gly Phe Gly Gly Ile Gly Gly
  1               5                  10

(2) INFORMATION FOR SEQ ID NO:18:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (B) LOCATION: 20...20
        (D) OTHER INFORMATION: where Xaa at position 20 is homoserine
            lactone (xi) SEQUENCE DESCRIPTION: SEQ ID NO:18:

Gly Gly Gly Pro Gly Gly Phe Gly Gly Ile Gly Gly Gly Ser Gly Gly
  1               5                  10                  15

Phe Gly Gly Xaa
                 20

(2) INFORMATION FOR SEQ ID NO:19:
```

(i) SEQUENCE CHARACTERISTICS:
            (A) LENGTH: 16 amino acids
            (B) TYPE: amino acid
            (D) TOPOLOGY: linear (ii) MOLECULE TYPE: peptide (ix) FEATURE:
            (B) LOCATION: 16...16
            (D) OTHER INFORMATION: where Xaa at position 16 is homoserine
                lactone (xi) SEQUENCE DESCRIPTION: SEQ ID NO:19:

Gly Gly Gly Leu Gly Gly Phe Gly Gly Ile Gly Gly Phe Gly Gly Xaa
  1               5                  10                  15

(2) INFORMATION FOR SEQ ID NO:20:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:20:

Gly Phe Gly Gly
  1

(2) INFORMATION FOR SEQ ID NO:21:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:21:

Gly Phe Gly Gly Met Gly Gly
  1               5

(2) INFORMATION FOR SEQ ID NO:22:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (B) LOCATION: 4...4
            (D) OTHER INFORMATION: Xaa = any amino acid (xi) SEQUENCE DESCRIPTION: SEQ ID NO:22:

Arg Gly Asp Xaa
  1

(2) INFORMATION FOR SEQ ID NO:23:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO:23:

Gly Ala Gly Ala Gly Ser 1           5

(2) INFORMATION FOR SEQ ID NO:24:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:24:

Ala Ser Ala Ala Ala Ala Ala Ala
1           5

(2) INFORMATION FOR SEQ ID NO:25:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:25:

Ser Ser Ala Ala Ala Ala Ala Ala Ala Ala
1           5                   10

(2) INFORMATION FOR SEQ ID NO:26:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:26:

Ala Ala Ala Ala Ala Ala Ala Ala
1           5

(2) INFORMATION FOR SEQ ID NO:27:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:27:

Val Pro Gly Val Gly
1           5

(2) INFORMATION FOR SEQ ID NO:28:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:28:

Val Pro Ala Val Gly
1           5

(2) INFORMATION FOR SEQ ID NO:29:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:29:

Val Pro Gly Gly
  1

(2) INFORMATION FOR SEQ ID NO:30:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (ix) FEATURE:
            (B) LOCATION: 1...4
            (D) OTHER INFORMATION: where Xaa at positions 1 through 4 may
                  be either Pro, Gly, Val, Gly; Gly, Val, Gly (one of the
                  Xaa's may be absent); Val, Gly (two of the Xaa's may be
                  absent); Gly (three of the Xaa's may be absent); or a
                  covalent bond
            (B) LOCATION: 10...13
            (D) OTHER INFORMATION: where Xaa at position 10 through 13
                  may be either Ile, Pro, Gly, Val; Ile, Pro, Gly (one of
                  the Xaa's may be absent); Ile, Pro (two of the Xaa's may
                  be absent); Ile (three of the Xaa's may be absent); or a
                  covalent bond (xi) SEQUENCE DESCRIPTION: SEQ ID NO:30:

Xaa Xaa Xaa Xaa Ile Pro Gly Val Gly Xaa Xaa Xaa Xaa
  1               5                  10

(2) INFORMATION FOR SEQ ID NO:31:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:31:

Pro Gly Val Gly
  1

(2) INFORMATION FOR SEQ ID NO:32:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:32:

Ile Pro Gly Val
  1

(2) INFORMATION FOR SEQ ID NO:33:

(i) SEQUENCE CHARACTERISTICS:
            (A) LENGTH: 10 amino acids
            (B) TYPE: amino acid
            (D) TOPOLOGY: linear

```
        (ii) MOLECULE TYPE: peptide (ix) FEATURE:
             (B) LOCATION: 6...7
             (D) OTHER INFORMATION: where Xaa at positions 6 and 7 is
                 hydroxyproline (trans-4-hydroxyproline, trans-3-hydroxy-
                 proline or trans-2,3-cis-3,4-dihydroxyproline)
             (B) LOCATION: 9...9
             (D) OTHER INFORMATION: where Xaa at position 9 is DOPA
                 (3,4-dihydroxyphenyl)-L-alanine (xi) SEQUENCE DESCRIPTION: SEQ ID NO:33:

Ala Lys Pro Ser Tyr Xaa Xaa Thr Xaa Lys
 1               5                  10

(2) INFORMATION FOR SEQ ID NO:34:

(i) SEQUENCE CHARACTERISTICS:
             (A) LENGTH: 10 amino acids
             (B) TYPE: amino acid
             (D) TOPOLOGY: linear (ii) MOLECULE TYPE: peptide (ix) FEATURE:
             (B) LOCATION: 6...7
             (D) OTHER INFORMATION: where Xaa at positions 6 and 7 is
                 hydroxyproline (trans-4-hydroxyproline, trans-3-hydroxy-
                 proline or trans-2,3-cis-3,4-dihydroxyproline)
             (B) LOCATION: 9...9
             (D) OTHER INFORMATION: where Xaa at position 9 is DOPA
                 (3,4-dihydroxyphenyl)-L-alanine (xi) SEQUENCE DESCRIPTION: SEQ ID NO:34:

Arg Lys Pro Ser Tyr Xaa Xaa Thr Xaa Lys
 1               5                  10

(2) INFORMATION FOR SEQ ID NO:35:

(i) SEQUENCE CHARACTERISTICS:
             (A) LENGTH: 10 amino acids
             (B) TYPE: amino acid
             (D) TOPOLOGY: linear (ii) MOLECULE TYPE: peptide (ix) FEATURE:
             (B) LOCATION: 6...7
             (D) OTHER INFORMATION: where Xaa at positions 6 and 7 is
                 hydroxyproline (trans-4-hydroxyproline, trans-3-hydroxy-
                 proline or trans-2,3-cis-3,4-dihydroxyproline)
             (B) LOCATION: 9...9
             (D) OTHER INFORMATION: where Xaa at position 9 is DOPA
                 (3,4-dihydroxyphenyl)-L-alanine (xi) SEQUENCE DESCRIPTION: SEQ ID NO:35:

Arg Lys Ile Ser Tyr Xaa Xaa Thr Xaa Lys
 1               5                  10

(2) INFORMATION FOR SEQ ID NO:36:

(i) SEQUENCE CHARACTERISTICS:
             (A) LENGTH: 10 amino acids
             (B) TYPE: amino acid
             (D) TOPOLOGY: linear (ii) MOLECULE TYPE: peptide (ix) FEATURE:
             (B) LOCATION: 6...7
             (D) OTHER INFORMATION: where Xaa at positions 6 and 7 is
                 hydroxyproline (trans-4-hydroxyproline, trans-3-hydroxy-
```

```
                    proline or trans-2,3-cis-3,4-dihydroxyproline)
          (B) LOCATION: 9...9
          (D) OTHER INFORMATION: where Xaa at position 9 is DOPA
              (3,4-dihydroxyphenyl)-L-alanine (xi) SEQUENCE DESCRIPTION: SEQ ID NO:36:

Arg Lys Thr Ser Tyr Xaa Xaa Thr Xaa Lys
 1               5                  10

(2) INFORMATION FOR SEQ ID NO:37:

(i) SEQUENCE CHARACTERISTICS:
         (A) LENGTH: 5 amino acids
         (B) TYPE: amino acid
         (D) TOPOLOGY: linear (ii) MOLECULE TYPE: peptide (xi) SEQUENCE DESCRIPTION: SEQ ID NO:37:

Gly Gln Gln Lys Gln
 1               5

(2) INFORMATION FOR SEQ ID NO:38:

(i) SEQUENCE CHARACTERISTICS:
         (A) LENGTH: 5 amino acids
         (B) TYPE: amino acid
         (D) TOPOLOGY: linear (ii) MOLECULE TYPE: peptide (xi) SEQUENCE DESCRIPTION: SEQ ID NO:38:

Gly Gly Val Gln Lys
 1               5

(2) INFORMATION FOR SEQ ID NO:39:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (ix) FEATURE:
         (B) LOCATION: 4...4
         (D) OTHER INFORMATION: Xaa = any amino acid (xi) SEQUENCE DESCRIPTION: SEQ ID NO:39:

Gly Gly Gly Xaa
 1

(2) INFORMATION FOR SEQ ID NO:40:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (ix) FEATURE:
         (B) LOCATION: 6...6
         (D) OTHER INFORMATION: Xaa = any amino acid (xi) SEQUENCE DESCRIPTION: SEQ ID NO:40:

Gly Gly Xaa Gly Gly Xaa
 1               5
```

(2) INFORMATION FOR SEQ ID NO:41:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (B) LOCATION: 9...9
        (D) OTHER INFORMATION: Xaa = any amino acid (xi) SEQUENCE DESCRIPTION: SEQ ID NO:41:

Gly Gly Phe Gly Gly Met Gly Gly Xaa
 1               5

(2) INFORMATION FOR SEQ ID NO:42:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (B) LOCATION: 3...3
        (D) OTHER INFORMATION: Xaa = any amino acid (xi) SEQUENCE DESCRIPTION: SEQ ID NO:42:

Gly Gly Xaa Gly Gly Phe Gly Gly Met
 1               5

(2) INFORMATION FOR SEQ ID NO:43:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (B) LOCATION: 1...20
        (D) OTHER INFORMATION: Xaa = any amino acid (xi) SEQUENCE DESCRIPTION: SEQ ID NO:43:

Gly Gly Gly Xaa Gly Gly Phe Gly Gly Ile Gly Gly Phe Gly Gly Met
 1               5                  10                  15

Gly Gly Gly Xaa
            20